(12) United States Patent
Ushiba et al.

(10) Patent No.: US 12,076,152 B2
(45) Date of Patent: Sep. 3, 2024

(54) ELECTROENCEPHALOGRAM DECISION SYSTEM, ELECTROENCEPHALOGRAM DECISION METHOD, PROGRAM, AND NON-TRANSITORY STORAGE MEDIUM

(71) Applicants: LIFESCAPES Inc., Tokyo (JP); Keio University, Tokyo (JP)

(72) Inventors: Junichi Ushiba, Kanagawa (JP); Koji Morikawa, Tokyo (JP)

(73) Assignees: LIFESCAPES Inc., Tokyo (JP); Keio University, Tokyo (JP)

(*) Notice: Subject to any disclaimer, the term of this patent is extended or adjusted under 35 U.S.C. 154(b) by 102 days.

(21) Appl. No.: 16/755,768

(22) PCT Filed: Oct. 19, 2018

(86) PCT No.: PCT/JP2018/038928
§ 371 (c)(1),
(2) Date: Apr. 13, 2020

(87) PCT Pub. No.: WO2019/078325
PCT Pub. Date: Apr. 25, 2019

(65) Prior Publication Data
US 2020/0253499 A1    Aug. 13, 2020

(30) Foreign Application Priority Data
Oct. 20, 2017    (JP) .................. 2017-204090

(51) Int. Cl.
*A61B 5/37* (2021.01)
*A61B 5/00* (2006.01)
(Continued)

(52) U.S. Cl.
CPC .............. *A61B 5/291* (2021.01); *A61B 5/374* (2021.01); *A61B 5/6803* (2013.01); *G06F 3/015* (2013.01)

(58) Field of Classification Search
None
See application file for complete search history.

(56) References Cited

U.S. PATENT DOCUMENTS

| | | | |
|---|---|---|---|
| 2015/0282760 A1* | 10/2015 | Badower | A61B 5/316 600/383 |
| 2016/0198971 A1 | 7/2016 | Yamada | |
| 2016/0220163 A1 | 8/2016 | Yamada | |
| 2017/0164857 A1* | 6/2017 | Soulet De Brugiere | A61B 5/6814 |

FOREIGN PATENT DOCUMENTS

| | | |
|---|---|---|
| JP | 2012-217721 A | 11/2012 |
| JP | 2015-127851 A | 7/2015 |

(Continued)

OTHER PUBLICATIONS

Hastie, T. et al., The Elements of Statistical Learning: Data Mining, Inference, and Prediction, Springer Series in Statistics, Second Edition, pp. 101-137 (Year: 2009).*

(Continued)

*Primary Examiner* — Sean P Dougherty
*Assistant Examiner* — Aurelie H Tu
(74) *Attorney, Agent, or Firm* — Renner, Otto, Boisselle & Sklar, LLP

(57) ABSTRACT

An electroencephalogram decision system determines, when finding electroencephalogram information representing an electroencephalogram obtained by an electrode unit placed on a region of interest that forms part of a subject's head satisfying a predetermined condition, that a target electroencephalogram, which is an electroencephalogram with a characteristic variation, should have been produced. The predetermined condition is selected from of detection conditions including a first type of condition and a second type of condition. The first type of condition specifies that a decision should be made, based on a component falling within a single frequency band included in the electroencephalogram represented by the electroencephalogram (Continued)

information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced.

12 Claims, 11 Drawing Sheets

(51) Int. Cl.
*A61B 5/291* (2021.01)
*A61B 5/374* (2021.01)
*G06F 3/01* (2006.01)

(56) References Cited

FOREIGN PATENT DOCUMENTS

| JP | 2016-013182 A | 1/2016 |
| JP | 2016-146173 A | 8/2016 |
| WO | 2011/123059 A1 | 10/2011 |
| WO | 2014/072564 A1 | 5/2014 |

OTHER PUBLICATIONS

International Search Report and Written Opinion for corresponding Application No. PCT/JP2018/038928, mailed Dec. 18, 2018.
Extended European Search Report for corresponding Application No. 18868564.8, dated Sep. 14, 2020.

* cited by examiner

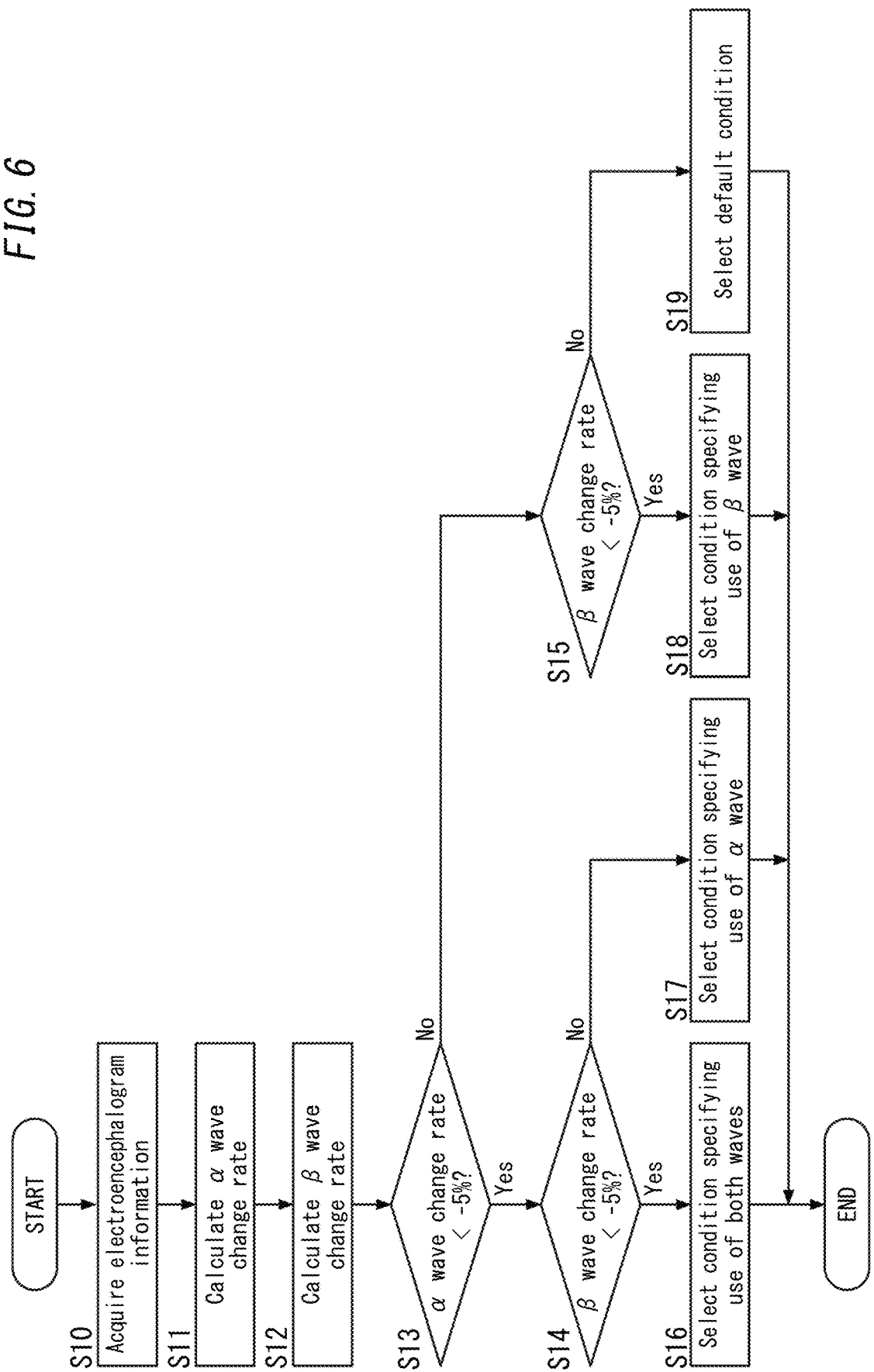

FIG. 8

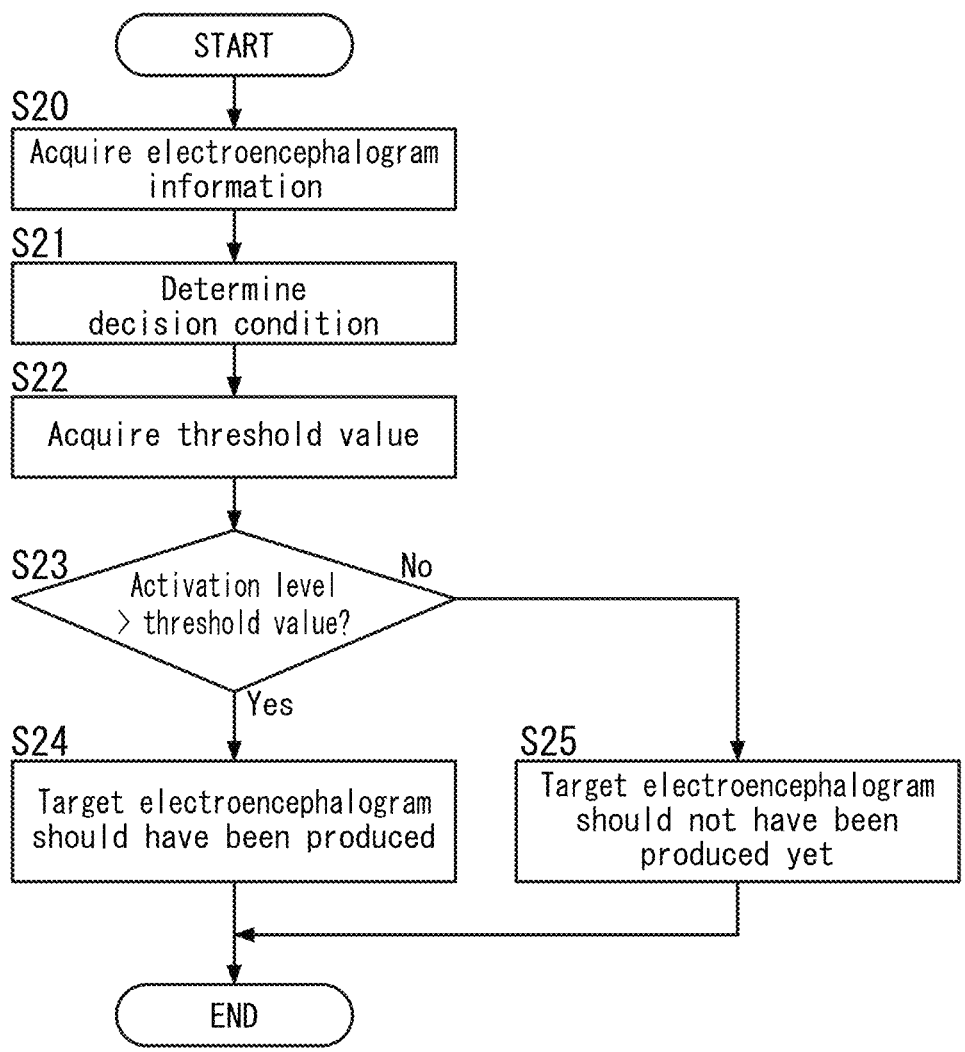

ELECTROENCEPHALOGRAM DECISION SYSTEM, ELECTROENCEPHALOGRAM DECISION METHOD, PROGRAM, AND NON-TRANSITORY STORAGE MEDIUM

TECHNICAL FIELD

The present disclosure generally relates to an electroencephalogram (EEG) decision system, an electroencephalogram decision method, a program, and a non-transitory storage medium. More particularly, the present disclosure relates to an electroencephalogram decision system, electroencephalogram decision method, program, and non-transitory storage medium, all of which are configured or designed to detect a target electroencephalogram based on electroencephalogram information representing a subject-specific electroencephalogram obtained by an electrode unit that is placed on a region of interest (ROI) forming part of the subject's head.

BACKGROUND ART

Patent Literature 1 discloses a rehabilitation system. The rehabilitation system includes an electroencephalograph, a presentation device, an electric gear, and a controller. The electroencephalograph measures a patient's electroencephalogram. The presentation device presents information to the patient to provide him or her with some feedback. The electric gear applies at least one of an electrical stimulus or a dynamic stimulus to the patient's body. The controller extracts an event-related desynchronization (ERD) signal related to his or her movement intention from the electroencephalogram measured by the electroencephalograph. When a decision is made that the movement intention has been expressed properly, the controller makes the presentation device and the electric gear provide the feedback.

According to Patent Literature 1, the ERD signal is obtained as a variation with time in the frequency power of an electroencephalogram. Specifically, if a variation in the frequency power at a particular frequency (e.g., a frequency of around 10 Hz) is observed continuously for a predetermined amount of time within a predetermined time range, a decision is made that the ERD signal has been detected. Nevertheless, the frequency band in which the power declines due to the event-related desynchronization, the magnitude of the decline in the power, and other parameters are not uniform but vary according to the patient's (or subject's) attributes (such as his or her age and sex), affected region, affected condition, and other individual differences. Therefore, the ERD signal (representing an electroencephalogram with a characteristic variation) is not determined uniformly but may vary from one patient to another.

CITATION LIST

Patent Literature

Patent Literature 1: JP 2016-13182 A

SUMMARY OF INVENTION

It is therefore an object of the present disclosure to provide an electroencephalogram decision system, an electroencephalogram decision method, a program, and a non-transitory storage medium, all of which contribute to improving the decision accuracy of electroencephalograms.

An electroencephalogram decision system according to an aspect of the present disclosure includes an acquisition unit and a detection unit. The acquisition unit acquires electroencephalogram information representing an electroencephalogram obtained by an electrode unit placed on a region of interest that forms part of a subject's head. The detection unit determines, when finding the electroencephalogram information acquired by the acquisition unit satisfying a decision condition, that a target electroencephalogram, which is an electroencephalogram with a characteristic variation, should have been produced. The decision condition is selected from a plurality of conditions. The plurality of conditions includes a first type of condition and a second type of condition. The first type of condition specifies that a decision should be made, based on a component falling within a single frequency band included in the electroencephalogram represented by the electroencephalogram information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced.

An electroencephalogram decision method according to another aspect of the present disclosure includes a first step and a second step. The first step includes acquiring electroencephalogram information representing an electroencephalogram obtained by an electrode unit placed on a region of interest that forms part of a subject's head. The second step includes making a decision, when finding the electroencephalogram information acquired in the first step satisfying a decision condition, that a target electroencephalogram, which is an electroencephalogram with a characteristic variation, should have been produced. The decision condition is selected from a plurality of conditions. The plurality of conditions includes a first type of condition and a second type of condition. The first type of condition specifies that a decision should be made, based on a component falling within a single frequency band included in the electroencephalogram represented by the electroencephalogram information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced.

A program according to still another aspect of the present disclosure is designed to cause a computer system to carry out the electroencephalogram decision method described above.

A non-transitory storage medium according to yet another aspect of the present disclosure is readable for a computer system and stores a program designed to cause the computer system to carry out the electroencephalogram decision method described above.

BRIEF DESCRIPTION OF DRAWINGS

FIG. 6 is a flowchart showing the procedure in which the electroencephalogram decision system performs selection processing during calibration processing;

FIG. 8 illustrates an exemplary calibration screen of the electroencephalogram decision system;

FIG. 12 is a flowchart showing the procedure in which the electroencephalogram decision system makes decision processing about the target electroencephalogram.

DESCRIPTION OF EMBODIMENTS

Embodiment

1 Overview

Figure 1:
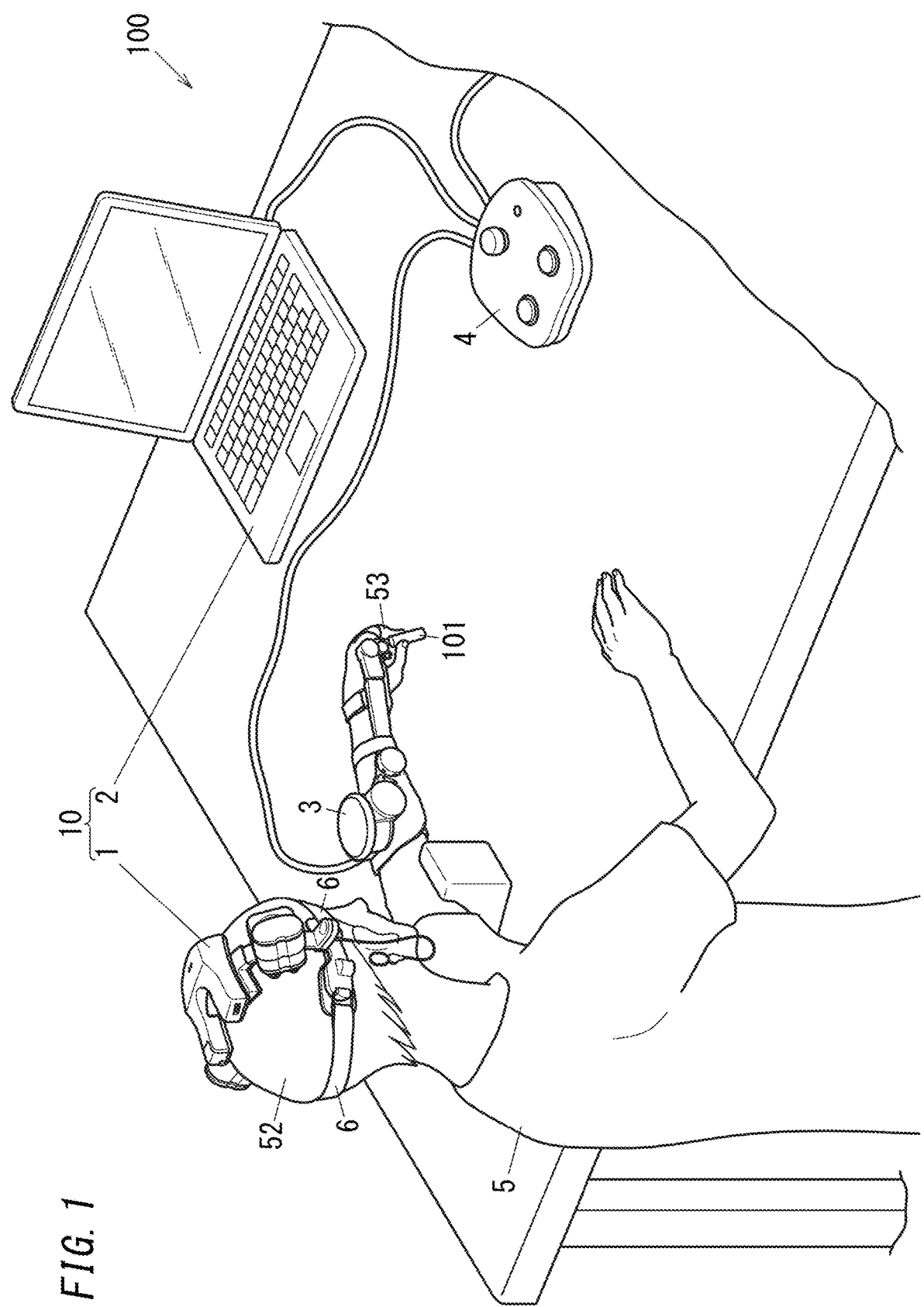
FIG. 1 schematically illustrates how an electroencephalogram decision system according to an embodiment and a rehabilitation support system including the electroencephalogram decision system may be used.

An overview of an electroencephalogram decision system 10 according to an embodiment will be described with reference to FIGS. 1 and 2.

The electroencephalogram decision system 10 according to this embodiment has the capability of an electroencephalogram measuring system for measuring an electroencephalogram specific to a subject 5, and acquires electroencephalogram information representing a subject-specific electroencephalogram obtained by an electrode unit 11 placed on a region of interest 51 that forms part of the subject's 5 head 52. As used herein, the "electroencephalogram (EEG)" refers to a waveform recorded by deriving, out of a human's body, electrical signals (action potentials) generated by (groups of) nerve cells (or neurons) of a human brain. Also, as used herein, an "electroencephalogram" refers to, unless otherwise stated, an on-scalp electroencephalogram recorded by the electrode unit 11, which the subject wears on his or her body surface, with respect to a comprehensive action potential of a great many groups of neurons (that form a neural network) of the cerebral cortex.

The electroencephalogram decision system 10 includes a headset 1 with the electrode unit 11 and an information processor 2. The headset 1 is worn by a subject 5 on his or her head 52 with the electrode unit 11 brought into contact with his or her head 52 surface (i.e., scalp). According to the present disclosure, the electrode unit 11 is mounted on paste (electrode paste) applied onto the surface of the head 52, and thereby comes into contact with the surface of the head 52. In this case, the electrode unit 11 comes into direct contact with (i.e., not via the subject's hairs) the surface of the head 52 by pushing the hairs aside. Naturally, the electrode unit 11 may come into direct contact with the surface of the head 52 with no paste applied between them. That is to say, according to the present disclosure, "to bring the electrode unit 11 into contact with the surface of the head 52" refers to not only bringing the electrode unit 11 into direct contact with the surface of the head 52 but also bringing the electrode unit 11 into indirect contact with the surface of the head 52 with some intermediate interposed between the electrode unit 11 and the surface of the head 52. The intermediate does not have to be paste but may also be a gel with electrical conductivity. The headset 1 measures the electroencephalogram specific to the subject 5 by having the electrode unit 11 measure and record the action potential of the subject's 5 brain, thereby generating electroencephalogram information representing the electroencephalogram. The headset 1 may transmit the electroencephalogram information to the information processor 2 by wireless communication, for example. In response, the information processor 2 subjects the electroencephalogram information acquired from the headset 1 to various types of processing, or displays the electroencephalogram information thereon.

In the following description of embodiments, a situation where the electroencephalogram decision system 10 is used in a rehabilitation support system 100 for supporting the subject 5 in his or her rehabilitation will be described. That is to say, the rehabilitation support system 100 includes the electroencephalogram decision system 10 according to this embodiment. The rehabilitation support system 100 further includes an exercise assisting device 3 and a controller 4. The exercise assisting device 3 assists the subject 5 with his or her exercise by applying at least one of a mechanical stimulus or an electrical stimulus to the subject 5. The controller 4 controls the exercise assisting device 3 based on the electroencephalogram information acquired by the electroencephalogram decision system 10.

This rehabilitation support system 100 supports a subject 5, who suffers from either a motor paralysis or a decline in motor function in some region of his or her body due to some brain disease such as cerebral apoplexy (stroke) or a traffic accident, in his or her rehabilitation by exercise therapy. Such a subject 5 may either be unable to do, or show a decline in the physical ability to do well, a voluntary movement, which is a movement that the subject 5 does of his or her own will or by intention. As used herein, the "exercise therapy" refers to a method for recovering a voluntary movement function for an affected region of the subject's 5 body by making the subject 5 exercise his or her region that is either unable to do, or shows a decline in the physical ability do well, such a voluntary movement (hereinafter referred to as "affected region").

In the following description of embodiments, the rehabilitation support system 100 is supposed to be used, for example, to support the subject 5 in his or her rehabilitation to recover the function of his or her left hand fingers 53. That is to say, in this case, the subject's 5 left hand fingers are his or her affected region. However, this is only an example and should not be construed as limiting. Alternatively, the rehabilitation support system 100 may also be used to support the subject 5 in his or her rehabilitation to recover the function of his or her right hand fingers.

The rehabilitation support system 100 supports the subject 5 in his or her voluntary movement by having the exercise assisting device 3, which the subject 5 wears on his or her left hand, apply at least one of a mechanical stimulus or an electrical stimulus to his or her left hand when the subject 5 does the voluntary movement using his or her left hand fingers 53. This allows, just like a situation where a medical staff such as a physical therapist or an occupational therapist supports the subject 5 in his or her voluntary movement by holding the subject's 5 hand fingers 53, the rehabilitation support system 100 to support him or her in the voluntary movement. Thus, the rehabilitation support system 100 is able to provide rehabilitation by exercise therapy as effectively as in a situation where some medical staff provides the support and even more effectively than in a situation where the subject 5 does the voluntary movement by him- or herself.

Meanwhile, to provide support for such rehabilitation, the rehabilitation support system 100 suitably assists, using the exercise assisting device 3, the subject 5 with his or her voluntary movement when the subject 5 is going to do the voluntary movement on his or her own. The rehabilitation support system 100 assists, when the subject 5 is going to do voluntary movement, him or her in the voluntary movement using the exercise assisting device 3 by operating the exercise assisting device 3 in coordination with the subject's 5 electroencephalogram (electroencephalogram information) measured by the electroencephalogram decision system 10. In other words, the rehabilitation support system 100 provides rehabilitation by exercise therapy by using the brain-machine interface (BMI) technology for operating a machine (such as the exercise assisting device 3) based on the brain activity (electroencephalogram).

When the subject 5 is going to do voluntary movement (i.e., while the subject 5 is doing the voluntary movement), a characteristic variation may arise in his or her electroencephalogram. That is to say, when the subject 5 plans to do (or imagines doing) the voluntary movement, a brain region corresponding to the region that should be exercised to do the voluntary movement may be activated. Examples of such brain regions include a somatosensory motor cortex. Supporting the subject 5 in his or her voluntary movement using the exercise assisting device 3 exactly at the timing when the brain region is activated would make the rehabilitation even more effective. Such brain region activation may be detected as a characteristic variation in electroencephalogram. Thus, the rehabilitation support system 100 starts supporting the subject 5 in his or her voluntary movement using the exercise assisting device 3 exactly at the timing when this characteristic variation arises in the electroencephalogram specific to the subject 5. Note that such a characteristic variation may arise in the electroencephalogram even if the voluntary movement is not actually carried out but when the subject 5 imagines doing the voluntary movement (i.e., plans to do the movement). That is to say, this characteristic variation may arise in the electroencephalogram even if the voluntary movement is not actually carried out but when the subject 5 plans to do, or imagines doing, the voluntary movement to activate the corresponding brain region. Therefore, the rehabilitation support system 100 may also support even a subject 5, who is unable to do the voluntary movement, in his or her attempt to do voluntary movement.

The rehabilitation support system 100 with such a configuration is able to provide effective rehabilitation by exercise therapy for the subject 5 while lightening the workload on medical staff. In addition, this rehabilitation support system 100 eliminates the variation in timing to start supporting the subject 5 in his or her voluntary movement due to a human factor such as the skill level of the medical staff who needs to support the subject 5 in his or her voluntary movement, thus reducing the variation in the effect of rehabilitation. In particular, the rehabilitation support system 100 is able to start supporting the subject 5 in his or her voluntary movement exactly at the timing when a characteristic variation arises in his or her specific electroencephalogram (i.e., the timing when the brain region is actually activated). As can be seen, this rehabilitation support system 100 allows the subject 5 to start training exactly at the timing when his or her brain activity starts, thus contributing to learning and establishing right brain activity. Among other things, it is difficult for even the subject 5 him- or herself and the medical staff to determine whether or not such a characteristic variation has arisen in his or her electroencephalogram. Thus, using this rehabilitation support system 100 provides highly effective rehabilitation that is usually difficult to realize by either the subject 5 or the medical staff alone.

In the embodiment to be described below, when the subject 5 uses the rehabilitation support system 100, the subject 5 is supposed to be accompanied by some medical staff such as a physical therapist or an occupational therapist and the rehabilitation support system 100 is supposed to be operated by the medical staff. However, the subject 5 who uses the rehabilitation support system 100 does not have to be accompanied by medical staff. Alternatively, the rehabilitation support system 100 may be operated by either the subject 5 him- or herself or his or her family member as well.

The electroencephalogram decision system 10 according to this embodiment is used in the rehabilitation support system 100 in order to detect an electroencephalogram as a target electroencephalogram with a characteristic variation that arises when the subject 5 is going to do the voluntary movement (i.e., when the subject 5 plans to do the voluntary movement). As will be described in detail later in the "(2) Rehabilitation support system" section, the electroencephalogram decision system 10 detects, as the characteristic variation, a variation caused due to event-related desynchronization (ERD) in the intensity of the electroencephalogram within a particular frequency band. As used herein, the "event-related desynchronization" refers to a decline in power falling within a particular frequency band of the electroencephalogram representing a brain wave measured in the vicinity of a motor area during the voluntary movement (or when the subject 5 just imagines doing the voluntary movement). As used herein, the phrase "during the voluntary movement" refers to a process that begins when the subject 5 plans to do (or imagines doing) the voluntary movement and ends when the voluntary movement is either done successfully or ends up in failure. The "event-related desynchronization" may be triggered, during the voluntary movement, by the subject's plan to do the voluntary movement (or his or her image of doing the voluntary movement). The frequency bands in which the event-related desynchronization causes a decline in power are mainly an α wave range (such as a frequency band from 8 Hz to less than 13 Hz) and a β wave range (such as a frequency band from 13 Hz to less than 30 Hz).

Nevertheless, the frequency band in which the event-related desynchronization causes a decline in power and the magnitude of the decline in power are not constant but vary according to the subject's 5 attributes (such as age and sex), affected region, affected condition, and other individual differences. Therefore, the electroencephalogram as the target of detection for the electroencephalogram decision system 10 (i.e., the electroencephalogram with a characteristic variation that may arise when the subject 5 plans to do the voluntary movement) is not determined uniformly but may vary from one subject 5 to another. Thus, the electroencephalogram decision system 10 is configured to analyze the electroencephalogram information, i.e., select a decision condition for detecting an electroencephalogram as a target from a plurality of conditions. The decision condition is determined by performing calibration processing for determining various types of parameters.

Figure 2:
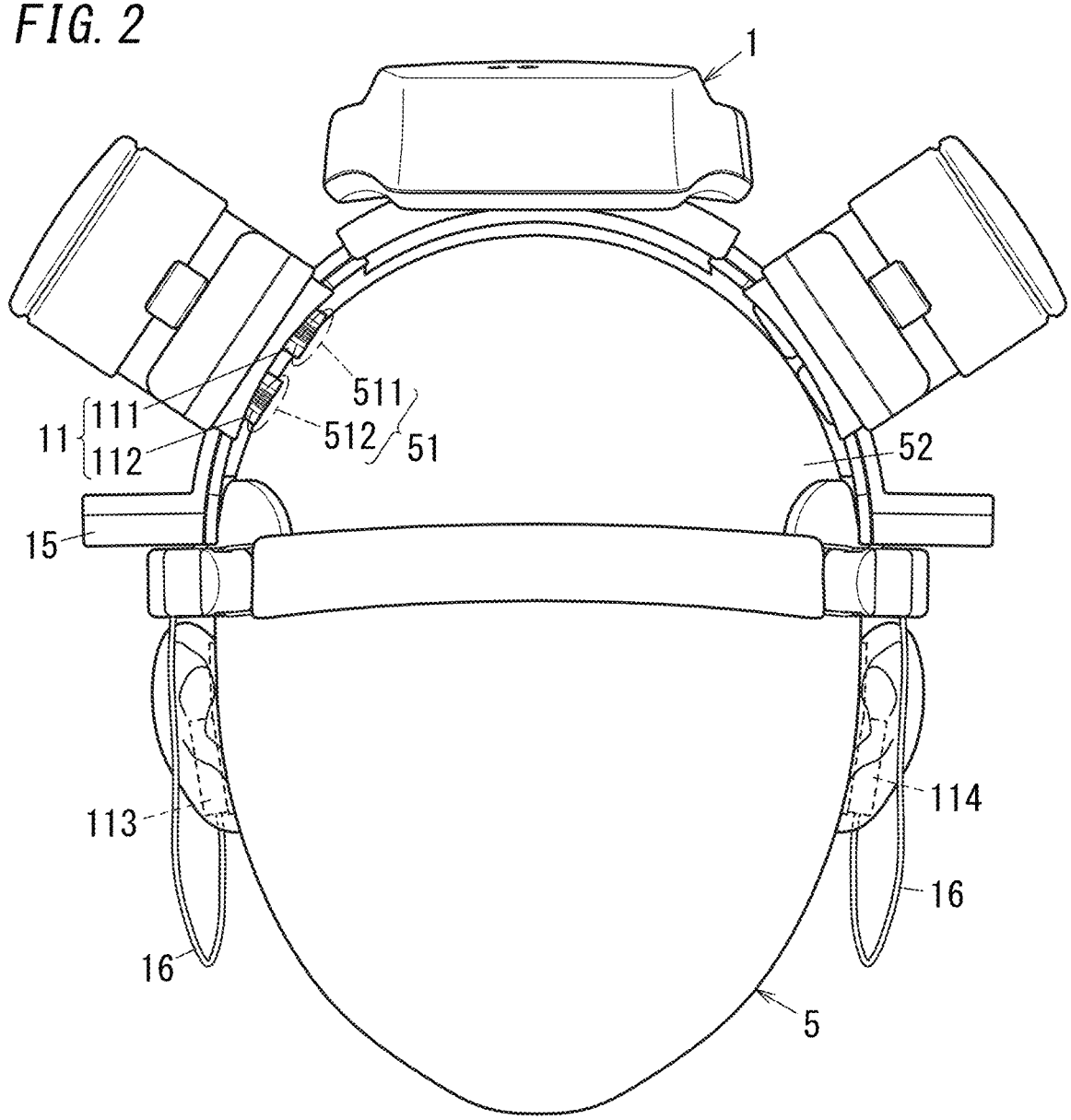
FIG. 2 is a schematic front view illustrating how the headset of the electroencephalogram decision system may be used.
Figure 3:
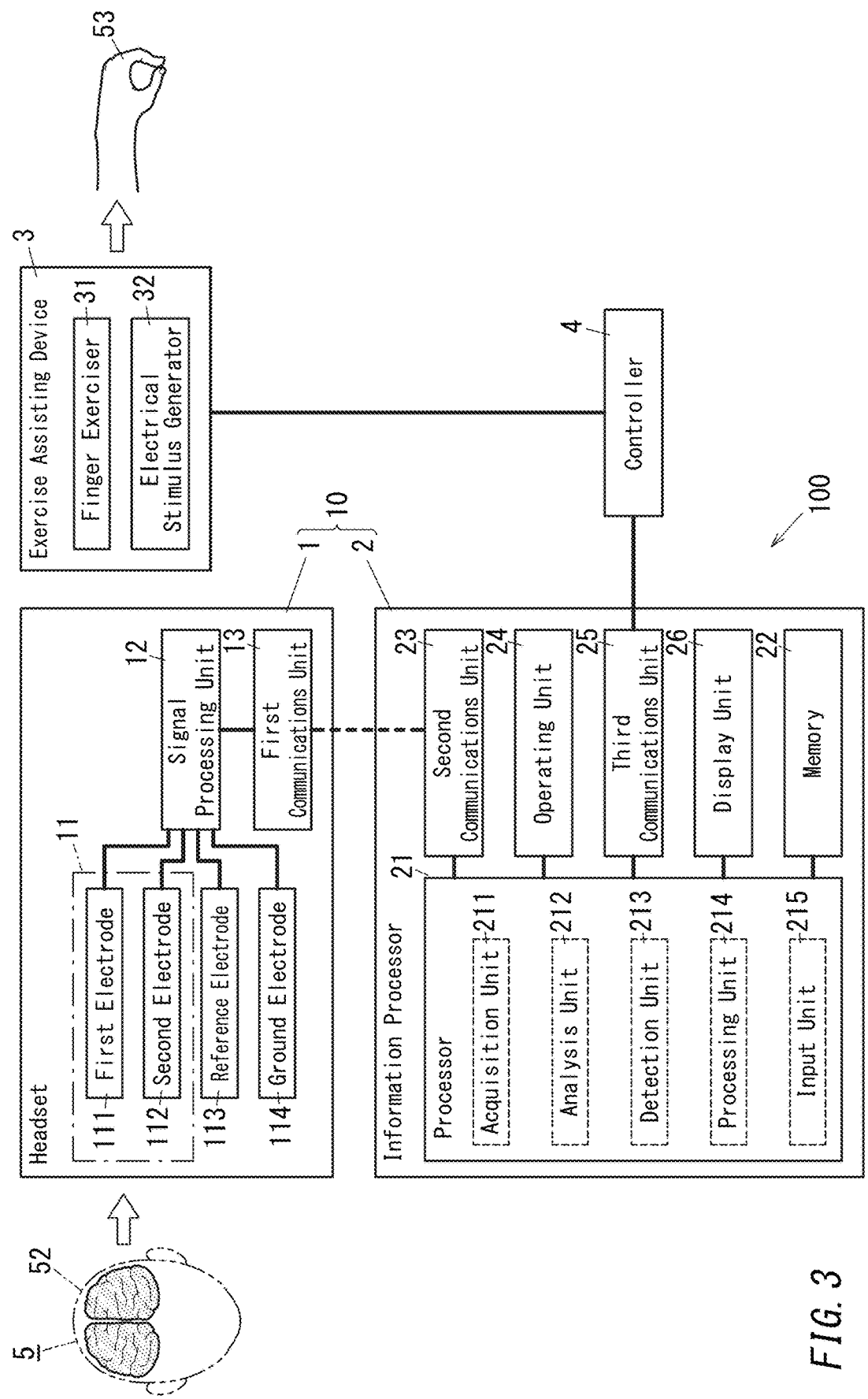
FIG. 3 is a block diagram illustrating a configuration for the electroencephalogram decision system and the rehabilitation support system.

An electroencephalogram decision system 10 according to this embodiment includes an acquisition unit 211 and a detection unit 213 as shown in FIG. 3. The acquisition unit 211 acquires electroencephalogram information representing an electroencephalogram obtained by an electrode unit 11 placed on a region of interest 51 that forms part of a subject's 5 head 52 (see FIG. 2). The detection unit 213 determines, when finding the electroencephalogram information acquired by the acquisition unit 211 satisfying a decision condition, that a target electroencephalogram, which is an electroencephalogram with a characteristic variation, should have been produced. The decision condition is selected from a plurality of conditions. The plurality of conditions includes a first type of condition and a second type of condition. The first type of condition specifies that a decision should be made, based on a component falling within a single frequency band included in the electroencephalogram represented by the electroencephalogram information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced. As described above, the target electroencephalogram (i.e., an electroencephalogram with a characteristic variation that may arise when the subject 5 plans to do voluntary movement) is not determined uniformly but varies from one subject 5 to another. In this electroencephalogram decision system 10, the decision condition is not fixed but is selected by the subject 5 from a plurality of conditions. As the plurality of conditions, a first type of condition that uses a component falling within a single frequency band and a second type of condition that uses, unlike the first type of condition, components falling within multiple different frequency bands are provided. This allows a condition suitable to each individual subject 5 to be used selectively. Thus, the electroencephalogram decision system 10 according to this embodiment is able to improve the decision accuracy of electroencephalograms.

2 Rehabilitation Support System

Next, a rehabilitation support system 100 according to this embodiment will be described in further detail.

As shown in FIG. 1, the rehabilitation support system 100 includes the electroencephalogram decision system 10, the exercise assisting device 3, and the controller 4.

As described above, the electroencephalogram decision system 10 according to this embodiment includes the headset 1 and the information processor 2.

As shown in FIG. 2, the headset 1 is worn by the subject 5 on his or her head 52. The headset 1 includes the electrode unit 11. The electrode unit 11 is placed on a region of interest 51, which forms part of the subject's 5 head 52. Specifically, the headset 1 has the subject's 5 electroencephalogram measured by the electrode unit 11 that is brought into contact with the region of interest 51 defined on an area of the surface (scalp) of the subject's 5 head 52, thereby generating electroencephalogram information representing the electroencephalogram.

The information processor 2 includes, as its main constituent element, a computer system such as a personal computer. The information processor 2 receives the electroencephalogram information from the headset 1 via wireless communication, and performs various types of processing on the electroencephalogram information. In this embodiment, detection of an electroencephalogram with a characteristic variation that may arise when the subject 5 plans to do (or imagines doing) the voluntary movement, the calibration processing, and other types of processing are performed by the information processor 2.

When the subject 5 plans to do (or imagines doing) the voluntary movement, the electroencephalogram measured usually comes to have a characteristic variation that represents a brain wave produced in the motor area corresponding to a body region where the voluntary movement is conducted. Thus, the electroencephalogram decision system 10 regards, as the target of measurement, the electroencephalogram detected from around the motor area corresponding to the affected region as the target of rehabilitation. In this case, the motor area corresponding to left hand fingers is located on the right side of the brain and the motor area corresponding to right hand fingers is located on the left side of the brain. That is why when the subject's 5 left hand fingers 53 are the target of rehabilitation as in this embodiment, the electroencephalogram recorded by the electrode unit 11 that is brought into contact with the right side of the subject's 5 head 52 is the target of measurement for this electroencephalogram decision system 10. That is to say, the electrode unit 11 is placed on a region of interest 51 that forms part of the right surface of the subject's 5 head 52 as shown in FIG. 2. For example, the electrode unit 11 is placed at a location designated by the mark "C4" according to the international 10-20 system. On the other hand, when the subject's 5 right hand fingers are the target of rehabilitation, the electrode unit 11 is placed on a region of interest that forms part of the left surface of the subject's 5 head 52. For example, the electrode unit 11 may be placed at a location designated by the mark "C3" according to the international 10-20 system in that case.

On detecting an electroencephalogram with a characteristic variation that may arise when the subject 5 plans to do voluntary movement, the electroencephalogram decision system 10 outputs a control signal for controlling the exercise assisting device 3. That is to say, in this rehabilitation support system 100, generation of a control signal for controlling the exercise assisting device 3 is triggered by detection by the electroencephalogram decision system 10 of an electroencephalogram with a characteristic variation that may arise when the subject 5 plans to do voluntary movement. Thus, this rehabilitation support system 100 allows the exercise assisting device 3 to assist the subject 5 with his or her voluntary movement when the subject 5 is going to do the voluntary movement. The electroencephalogram decision system 10 will be described in further detail later in the "(3) Electroencephalogram decision system" section.

The exercise assisting device 3 is a device for assisting the subject 5 with his or her exercise by applying at least one of a mechanical stimulus or an electrical stimulus to the subject 5. In this embodiment, the rehabilitation support system 100 is used to support the subject 5 in his or her rehabilitation to recover the function of his or her left hand fingers, and therefore, the exercise assisting device 3 is worn by the subject 5 on his or her left hand as shown in FIG. 1.

In the following description of this embodiment, the rehabilitation support system 100 is supposed to be used, for example, to support the subject 5 in his or her rehabilitation to recover the function of gripping something with his or her left hand fingers and the function of stretching his or her left hand fingers. As used herein, the "gripping action" refers to the action of gripping something. Also, as used herein, the "stretching action" refers to the action of opening a hand by stretching four hand fingers 53 (namely, second to fifth hand fingers), except the first hand finger (i.e., the thumb), or the action of releasing an "object" that the subject 5 is gripping through the gripping action. That is to say, in the case of this subject 5, his or her left hand fingers are the affected region, and the rehabilitation support system 100 is used to support the subject 5 in his or her rehabilitation to recover the ability to do voluntary movement, namely, the ability to grip something with his or her left hand fingers and the ability to stretch his or her left hand fingers. Actually, however, the rehabilitation support system 100 does not directly support the subject 5 in his or her gripping action but indirectly supports him or her in the attempt (rehabilitation) to recover the ability to grip something by assisting the subject 5 with his or her action of stretching hand fingers.

Thus, the rehabilitation support system 100 supports the subject 5, who is doing the stretching action as the voluntary movement, in his or her voluntary movement by making the exercise assisting device 3 worn by the subject 5 on his or her left hand apply at least one of a mechanical stimulus or an electrical stimulus to the subject's 5 left hand fingers 53. Specifically, the exercise assisting device 3 includes a finger exerciser 31 and an electrical stimulus generator 32 as shown in FIG. 3.

The finger exerciser 31 is a device for moving four hand fingers 53 (namely, the second to fifth hand fingers), except the first hand finger (thumb), by holding the four hand fingers 53 and applying a mechanical stimulus (external force) to these four hand fingers 53. The finger exerciser 31 includes a power source such a motor or a solenoid, and is configured to move the four hand fingers 53 by transmitting the force generated by the power source to the four hand fingers 53. The finger exerciser 31 is able to do two types of operations, namely, an "opening operation" of moving the four hand fingers 53 held away from the first finger (i.e., stretching the four hand fingers 53) and a "closing operation" of moving the four hand fingers 53 toward the first finger (i.e., making the hand fingers 53 grip something). The finger exerciser's 31 opening operation assists the subject 5 with his or her stretching action, and the finger exerciser's 31 closing operation assists the subject 5 with his or her gripping action.

The electrical stimulus generator 32 is a device for applying an electrical stimulus to the subject's 5 region for moving his or her hand fingers 53. In this case, the subject's 5 region for moving his or her hand fingers 53 includes a region corresponding to at least one of a muscle or a nerve of the subject's 5 hand fingers 53. For example, the subject's 5 region for moving his or her hand fingers 53 may be a part of the subject's 5 right or left arm. The electrical stimulus generator 32 includes a pad to be attached to the subject's 5 body (such as his or her right or left arm). The electrical stimulus generator 32 applies a stimulus to the region for moving the hand fingers 53 by applying an electrical stimulus (in the form of an electrical current) from the pad to the subject's 5 body.

The controller 4 controls the exercise assisting device 3 in accordance with the electroencephalogram information acquired by the electroencephalogram decision system 10. In this embodiment, the controller 4 is electrically connected to the information processor 2 of the electroencephalogram decision system 10 and the exercise assisting device 3. A power cable for supplying operating power to the exercise assisting device 3 and the controller 4 is connected to the controller 4. The controller 4 includes a driver circuit for driving the finger exerciser 31 of the exercise assisting device 3 and an oscillator circuit for driving the electrical stimulus generator 32. The controller 4 receives a control signal from the information processor 2 via wired communication, for example.

On receiving a first control signal from the information processor 2, the controller 4 makes its driver circuit drive the finger exerciser 31 of the exercise assisting device 3, thereby controlling the exercise assisting device 3 such that the finger exerciser 31 performs the "opening operation." Also, on receiving a second control signal from the information processor 2, the controller 4 makes its driver circuit drive the finger exerciser 31 of the exercise assisting device 3, thereby controlling the exercise assisting device 3 such that the finger exerciser 31 performs the "closing operation." Furthermore, on receiving a third control signal from the information processor 2, the controller 4 makes its oscillator circuit drive the electrical stimulus generator 32 of the exercise assisting device 3, thereby controlling the exercise assisting device 3 such that an electrical stimulus is applied to the subject's 5 body.

This allows the controller 4 to control the exercise assisting device 3 based on the electroencephalogram information acquired by the electroencephalogram decision system 10 by controlling the exercise assisting device 3 in accordance with the control signals supplied from the electroencephalogram decision system 10. Optionally, the controller 4 may also control the exercise assisting device 3 such that the finger exerciser 31 performs the "opening operation" and the "closing operation" in response to a turn of an operating switch provided for the controller 4.

Next, it will be described how to use this rehabilitation support system 100. In the following description of this embodiment, it will be described how the rehabilitation support system 100 supports the subject 5 in his or her voluntary movement (i.e., the stretching action) to be done by the subject 5 in order to release a peg 101 (see FIG. 1) from his or her left hand by stretching the hand fingers 53 from a position where he or she is gripping the peg 101 with his or her left hand fingers.

First, as a preparation process, the subject 5 wears the headset 1 on the head 52 and also wears the exercise assisting device 3 on his or her left hand. In this case, the subject 5 wears the headset 1 on his or her head 52 such that at least the electrode unit 11 is brought into contact with a part of the right surface of the subject's 5 head 52, which constitutes the region of interest 51. The exercise assisting device 3 is worn by the subject 5 so as to hold at least the four hand fingers 53 (i.e., the second to fifth hand fingers), except the first finger (thumb), of the subject's 5 left hand and attach the pad to the subject's 5 left arm. The headset 1 and the exercise assisting device 3 may be firmly fixed as appropriate so as not to be displaced or come loose during the rehabilitation. In the preparation process, the subject's 5 four hand fingers 53 are held by the finger exerciser 31 of the exercise assisting device 3 to make the subject 5 keep gripping the peg 101 with his or her left hand fingers. The subject 5 may be equipped with the headset 1 and the exercise assisting device 3 by either the subject 5 him- or herself or a medical staff.

When the preparation is done to make the headset 1 and the information processor 2 ready to communicate with each other, the electroencephalogram information generated by the headset 1 may be acquired by the information processor 2. That is to say, the electroencephalogram decision system 10 may acquire, at the information processor 2, the electroencephalogram information representing an electroencephalogram obtained by the electrode unit 11 placed on the region of interest 51 that forms part of the subject's 5 head 52. As will be described in detail later in the "(3) Electroencephalogram decision system" section, the information processor 2 makes its memory 22 (see FIG. 3) store (accumulate), along the time axis, the electroencephalogram information acquired. In addition, the information processor 2 generates a power spectrum of the electroencephalogram by carrying out a time frequency analysis on the electroencephalogram information stored, for example. This allows the electroencephalogram decision system 10 to detect an electroencephalogram with a characteristic variation that may arise when the subject 5 plans to do voluntary movement by making the information processor 2 constantly monitor the data of the power spectrum.

In this case, before the subject 5 starts his or her rehabilitation, the electroencephalogram decision system 10 performs calibration processing for determining various types of parameters for use to detect an electroencephalogram as the target of detection. This allows the electroencephalogram decision system 10 to improve the accuracy of detecting the electroencephalogram as the target of detection with variations from one subject 5 to another, in, for example, the frequency band where the power declines due to the event-related desynchronization and the magnitude of the decline in power, taken into account. The calibration processing will be described in further detail later in the "(3) Electroencephalogram decision system" section.

After having finished the preparation process including the calibration processing, the rehabilitation support system 100 starts performing a training process for supporting the subject 5 in his or her rehabilitation. In the training process, the subject 5 is supported in his or her rehabilitation based on the electroencephalogram measured by the electroencephalogram decision system 10 during a training period. Specifically, the training period is subdivided into two periods, namely, a rest period and an exercise period. In each of the rest period and the exercise period, the subject 5 undergoes his or her rehabilitation in accordance with the instructions given by the rehabilitation support system 100. In this embodiment, the training period may be 10 seconds, and if the training period is evenly divided into two, then the first half of 5 seconds is supposed to be the "rest period" and the second half of 5 seconds is supposed to be the "exercise period."

In the rest period, the subject 5 puts his or her body at rest (i.e., does not plan to do (or imagine doing) any voluntary movement) to keep relaxed. At this time, the electroencephalogram decision system 10 does not detect any electroencephalogram with a characteristic variation that may arise due to the event-related desynchronization when the subject 5 plans to do the voluntary movement.

Meanwhile, in the exercise period, the subject 5 plans to do (or imagines doing) the action of stretching the hand fingers 53 as a type of voluntary movement. At this time, the electroencephalogram decision system 10 may detect an electroencephalogram with a characteristic variation that may arise due to the event-related desynchronization when the subject 5 plans to do the voluntary movement. In this embodiment, such a characteristic variation in electroencephalogram is detected by comparing an activation level with a threshold value and determining whether or not the activation level is greater than the threshold value. As used herein, the "activation level" refers to a value representing the magnitude of decline in power (i.e., power spectrum) in a particular frequency band. When the event-related desynchronization causes a decline in power in the particular frequency band, the activation level exceeds the threshold value. Thus, the electroencephalogram decision system 10 detects the characteristic variation in electroencephalogram when finding the activation level greater than the threshold value.

In this electroencephalogram decision system 10, generation of a control signal for controlling the exercise assisting device 3 is triggered by the detection of the electroencephalogram with such a characteristic variation. This allows, when the subject 5 plans to do voluntary movement, the rehabilitation support system 100 to make the exercise assisting device 3 assist the subject 5 with the voluntary movement exactly at the timing when a brain region, corresponding to the target region of the voluntary movement, is actually activated.

The operation of the electroencephalogram decision system 10 during the training process will be described in further detail later in the "(3) Electroencephalogram decision system" section.

3 Electroencephalogram Decision System 3.1 Configuration

The electroencephalogram decision system 10 according to this embodiment will be described in further detail.

As shown in FIG. 3, the electroencephalogram decision system 10 includes: the headset 1 to be worn by the subject 5 on his or her head 52; and the information processor 2 including, as a major constituent element, a computer system such as a personal computer.

The headset 1 includes: the electrode unit 11; a signal processing unit 12; and a first communications unit 13. The headset 1 may be driven by a battery, for example, which supplies power for operating the signal processing unit 12 and the first communications unit 13.

The electrode unit 11 includes electrodes for measuring and recording the subject's 5 electroencephalogram (in the form of an electroencephalogram signal), which may be silver-silver chloride electrodes, for example. The electrode unit 11 may also be made of gold, silver, or platinum, for example. The electrode unit 11 includes a first electrode 111 and a second electrode 112. In this embodiment, the region of interest 51 set on the surface of the subject's 5 head 52 includes a first region of interest 511 and a second region of interest 512 as shown in FIG. 2. The first electrode 111 corresponds to, and is placed on, the first region of interest 511. The second electrode 112 corresponds to, and is placed on, the second region of interest 512. Specifically, the first region of interest 511 and the second region of interest 512 are arranged in this order on a line segment connecting the median center of the head 52 to the subject's 5 right ear such that the first region of interest 511 is located closer to the median center than (i.e., located over) the second region of interest 512 is.

Also, in this embodiment, the headset 1 further includes a reference electrode 113 and a ground electrode 114. The reference electrode 113 is an electrode for measuring the reference potential of the electroencephalogram signal to be measured by each of the first electrode 111 and the second electrode 112. The reference electrode 113 is arranged behind either the right ear or the left ear of the head 52. Specifically, the reference electrode 113 is arranged behind the ear, on which the first electrode 111 and the second electrode 112 are placed, on the head 52. In this embodiment, the first electrode 111 and the second electrode 112 are placed on the right surface of the head 52, and therefore, the reference electrode 113 is arranged behind the right ear. On the other hand, the ground electrode 114 is arranged behind the right or left ear, on which the reference electrode 113 is not placed, on the head 52. In this embodiment, the reference electrode 113 is arranged behind on the right ear, and therefore, the ground electrode 114 is arranged behind the left ear. Each of the reference electrode 113 and the ground electrode 114 is electrically connected to the body 15 of the headset 1 via electric wires 16 (see FIG. 2) and is attached to the surface of the head 52 (i.e., the scalp). Optionally, the reference electrode 113 and the ground electrode 114 do not have to be placed behind the right or left ear but may also be placed on the right or left earlobe. In any case, the region behind the right or left ear and the right or left earlobe are regions of the head that are not easily affected by a bioelectric potential deriving from a brain activity. In other words, the reference electrode 113 and the ground electrode 114 are suitably arranged in such regions of the head that are not easily affected by a bioelectric potential deriving from the brain activity.

The signal processing unit 12 is electrically connected to the electrode unit 11, the reference electrode 113, and the ground electrode 114 to perform signal processing on the electroencephalogram signal (electrical signal) supplied from the electrode unit 11 and generate electroencephalogram information. That is to say, the headset 1 detects the subject's 5 electroencephalogram by having the electrode unit 11 measure the activity potential of the subject's 5 brain, to make the signal processing unit 12 generate electroencephalogram information representing the electroencephalogram. The signal processing unit 12 includes at least an amplifier for amplifying the electroencephalogram signal and an A/D converter for converting an analog electroencephalogram signal into a digital signal, and outputs, as the electroencephalogram information, the amplified digital electroencephalogram signal.

The first communications unit 13 has the capability of communicating with the information processor 2. The first communications unit 13 transmits, to the information processor 2, at least the electroencephalogram information generated by the signal processing unit 12. In this embodiment, the first communications unit 13 is able to communicate with the information processor 2 bidirectionally. The communications protocol of the first communications unit 13 may be wireless communication compliant with the Bluetooth® standard. The electroencephalogram information is transmitted, as needed, from the first communications unit 13 to the information processor 2.

The information processor 2 includes, as its major constituent element, a computer system including a processor 21 and a memory 22. The information processor 2 further includes a second communications unit 23, an operating unit 24, a third communications unit 25, and a display unit 26.

The second communications unit 23 has the capability of communicating with (the first communications unit 13 of) the headset 1. The second communications unit 23 receives at least the electroencephalogram information from the headset 1. In this embodiment, the second communications unit 23 is able to communicate with the headset 1 bidirectionally. The second communications unit 23 receives, as needed, the electroencephalogram information, sampled at a sample frequency of about 200 Hz, for example, from the headset 1.

The third communications unit 25 has the capability of communicating with the controller 4. The third communications unit 25 transmits at least a control signal to the controller 4. The communications protocol of the third communications unit 25 is a wired communication compliant with the universal serial bus (USB) standard.

In this embodiment, the information processor 2 is equipped with a touchscreen panel display, which functions as the operating unit 24 and the display unit 26. Thus, the information processor 2 determines, when the operating unit 24 detects any of various types of operations (including tapping, swiping, and dragging) on buttons and other objects on the screen of the display unit 26, that the buttons and other objects should have been operated. That is to say, the operating unit 24 and the display unit 26 function as a user interface that not only displays various types of information thereon but also accepts operating commands entered by either the subject 5 or a medical staff. Note that the operating unit 24 does not have to be implemented as a touchscreen panel display but may also be implemented as a keyboard, a pointing device, a mechanical switch, or any other type of input device.

The processor 21 has various functions serving as an acquisition unit 211, an analysis unit 212, a detection unit 213, a processing unit 214, and an input unit 215. The respective functions of the acquisition unit 211, analysis unit 212, detection unit 213, processing unit 214, and input unit 215 are performed by having a program stored in the memory 22 executed by the processor 21.

The acquisition unit 211 acquires electroencephalogram information representing an electroencephalogram obtained by the electrode unit 11 placed on the region of interest 51 that forms part of the subject's 5 head 52. That is to say, the acquisition unit 211 acquires, from the headset 1 and via the second communications unit 23, the electroencephalogram information representing the electroencephalogram obtained by the electrode unit 11 of the headset 1. Specifically, in this embodiment, the acquisition unit 211 acquires first electroencephalogram information representing the electroencephalogram obtained by the first electrode 111 and second electroencephalogram information representing the electroencephalogram obtained by the second electrode 112. That is to say, in this embodiment, the electrode unit 11 includes the first electrode 111 and the second electrode 112. Thus, the acquisition unit 211 regards the electroencephalogram information collected by the first electrode 111 and the electroencephalogram information collected by the second electrode 112 as the first electroencephalogram information and the second electroencephalogram information, respectively. In this embodiment, the acquisition unit 211 acquires electroencephalogram information in a digital form and stores, in the memory 22, the electroencephalogram information thus acquired. At this time, the time-series data of the electroencephalogram information collected by the electroencephalogram decision system 10 since the beginning through the end of the training period is stored in the memory 22.

The analysis unit 212 analyzes the electroencephalogram information acquired by the acquisition unit 211. The analysis unit 212 performs a frequency analysis on the electroencephalogram information stored in the memory 22, thereby generating spectrum data representing the signal intensity on a frequency band basis. Specifically, the analysis unit 212 reads pieces of the electroencephalogram information, corresponding to a predetermined period of time, from the memory 22 and carries out a frequency analysis such as a short-time Fourier transform (STFT) on the pieces of the electroencephalogram information. This allows the power to be calculated on a frequency band basis with respect to the electroencephalogram signal that varies with time. As used herein, the "power" refers to an integrated value of the intensities on a frequency band basis (i.e., spectrum intensities).

The detection unit 213 determines, when finding the electroencephalogram information acquired by the acquisition unit 211 satisfying a decision condition, that a target electroencephalogram, which is an electroencephalogram with a characteristic variation, should have been produced. The decision condition is selected from a plurality of conditions. In this embodiment, the plurality of conditions includes first to fourth detection conditions. The first detection condition is a condition specifying that the target electroencephalogram should be detected based on components falling within first and second frequency bands. The second detection condition is a condition specifying that the target electroencephalogram should be detected based on a component falling within the first frequency band, not the second frequency band. The third detection condition is a condition specifying that the target electroencephalogram should be detected based on a component falling within the second frequency band, not the first frequency band. The fourth detection condition is a condition specifying that the target electroencephalogram should be detected based on components falling within two preselected frequency bands. This increases the chances of any one of the plurality of conditions being a decision condition suitable to each individual subject.

The first frequency band is an α-wave frequency band, which may be a range from 8 Hz to less than 13 Hz, for example. The second frequency band is a β-wave frequency band, which may be a range from 13 Hz to less than 30 Hz, for example. In this embodiment, the first detection condition is a condition specifying that the α wave and the β wave should be both used. The second detection condition is a condition specifying that only the α wave should be used out of the two waves. The third detection condition is a condition specifying that only the β wave should be used out of the two waves. This improves the decision accuracy of an electroencephalogram with a characteristic variation that may arise when the subject 5 plans to do voluntary movement.

The two frequency bands according to the fourth detection condition are selected based on a healthy person's electroencephalogram, and may be a first band (e.g., a range from 8 Hz to less than 10 Hz) included in the α-wave frequency band and a second band (e.g., a range from 14 Hz to less than 16 Hz) included in the β-wave frequency band. The first and second bands according to the fourth detection condition are set irrespective of the subject's 5 electroencephalogram. It can be said that the fourth detection condition is a default condition. Adopting the fourth detection condition improves the decision accuracy of electroencephalograms while using a healthy person's electroencephalogram as a reference. As used herein, the "healthy person" refers to a person who does not suffer from a motor paralysis or a decline in motor function in any region of his or her body due to some brain disease such as cerebral apoplexy (stroke) or a traffic accident.

The plurality of conditions such as these includes first, second, and third types of conditions. The first type of condition specifies that a decision should be made, based on a component falling within a single frequency band included in the electroencephalogram represented by the electroencephalogram information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced. The third type of condition specifies that a decision should be made, based on a component falling within one or more frequency bands selected according to a healthy person's electroencephalogram, whether or not the target electroencephalogram has been produced. In this embodiment, the second detection condition and the third detection condition correspond to a first type of conditions and the first detection condition corresponds to the second type of condition. The fourth detection condition corresponds to the third type of condition. Note that the third type of condition may correspond to either the first type of condition or the second type of condition depending on the number of frequency bands selected.

The detection unit 213 uses, as the electroencephalogram information acquired by the acquisition unit 211, the power on the frequency band basis analyzed by the analysis unit 212. That is to say, the detection unit 213 detects, based on the power on the frequency band basis that has been analyzed by the analysis unit 212, an electroencephalogram with a characteristic variation that may arise when the subject 5 plans to do the voluntary movement. Specifically, the detection unit 213 detects either the presence or absence of an electroencephalogram with the characteristic variation by determining whether the power in the particular frequency band falls within a rest range or an exercise range. As used herein, the "rest range" refers to a range in which the power falling within a particular frequency band of the subject's 5 electroencephalogram may take when the subject 5 puts his or her body at rest, i.e., plans to do (or imagines doing) no voluntary movement and keeps relaxed. In other words, it can be said that the rest range is a range in which components within the first and second frequency bands of the subject's 5 electroencephalogram may fall when the subject 5 puts his or her body at rest. On the other hand, the "exercise range" as used herein refers to a range in which the power falling within the particular frequency band of the electroencephalogram may take when the subject 5 plans to do the voluntary movement. In other words, it can be said that the exercise range is a range in which components within the first and second frequency bands of the subject's 5 electroencephalogram may fall when the subject 5 plans to do some voluntary movement. That is to say, the detection unit 213 determines, when finding that the power falling within the particular frequency band has made a transition from the rest range to the exercise range, that an electroencephalogram with a characteristic variation that may arise when the subject 5 plans to do the voluntary movement should have been produced. In other words, the detection unit 213 determines, by seeing the components within the first and second frequency bands make a transition from the rest range to the exercise range, that the target electroencephalogram should have been produced according to the first detection condition.

Figure 4:
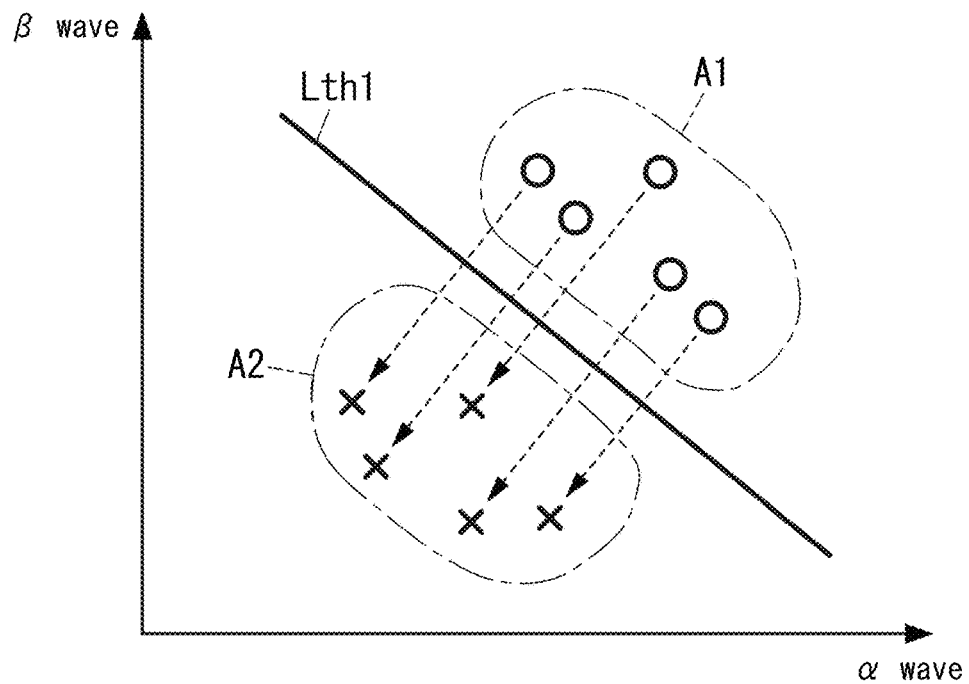
FIG. 4 is a graph showing how to determine a threshold value with respect to an activation level of the electroencephalogram decision system.
Figure 5A:
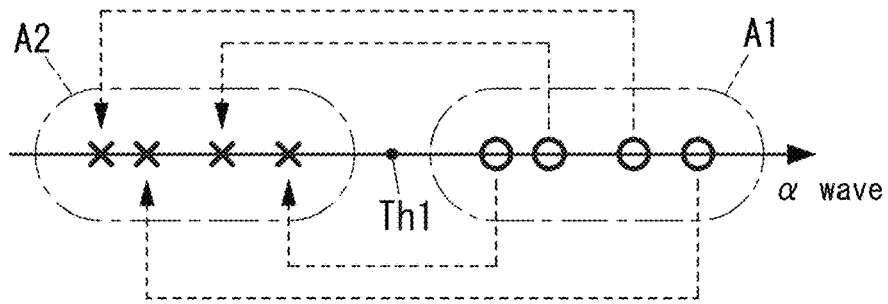
FIGS. 5A and 5B are real number lines illustrating how to determine a threshold value with respect to the activation level of the electroencephalogram decision system.
Figure 5B:
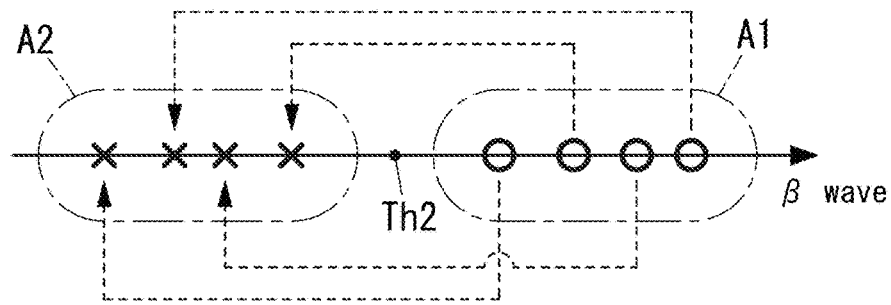

More specifically, according to this embodiment, the detection unit 213 may calculate, based on the power on the frequency band basis analyzed by the analysis unit 212, an activation level indicating the magnitude of decline in power in the particular frequency band, for example. Then, the detection unit 213 compares the activation level calculated with a threshold value stored in the memory 22, and determines, when finding the activation level greater than the threshold value, that the characteristic variation should have arisen in the electroencephalogram. That is to say, the threshold value with respect to the activation level is a value, in a graph representing the power in the particular frequency band (see FIG. 4), corresponding to the border line (or the line Lth1) between the rest range A1 and the exercise range A2. Thus, when the event-related desynchronization causes a decline in the power of the particular frequency band to have the power falling within the particular frequency band make a transition from the rest range to the exercise range, the activation level exceeds the threshold value. FIG. 4 illustrates a situation where two frequency bands, namely, a first frequency band (α-wave frequency band) and a second frequency band (β-wave frequency band), are selected as particular frequency bands (i.e., when either the first detection condition or the fourth detection condition is selected). FIGS. 5A and 5B are real number lines representing powers falling within the particular frequency bands. FIG. 5A illustrates a situation where the first frequency band (i.e., the β-wave frequency band) is selected as a particular frequency band (under the second detection condition). In this case, the threshold value with respect to the activation level corresponds to the border (point Th1) between the rest range A1 and the exercise range A2. FIG. 5B illustrates a situation where the second frequency band (i.e., the β-wave frequency band) is selected as a particular frequency band (under the third detection condition). In this case, the threshold value with respect to the activation level corresponds to the border (point Th2) between the rest range A1 and the exercise range A2. As will be described in detail later in the "(3.3) Calibration processing" section, the threshold value is set through the calibration processing.

The processing unit 214 carries out the calibration processing to determine the parameters for use to analyze the electroencephalogram information. That is to say, the processing unit 214 carries out the calibration processing to determine various types of parameters including at least the threshold value with respect to the activation level. In this embodiment, the calibration processing includes selection processing for selecting a decision condition from a plurality of conditions based on the electroencephalogram information acquired by the acquisition unit 211. That is to say, the decision condition for use in the detection unit 213 is determined by the processing unit 214. This allows a decision condition suitable to each individual subject to be selected from a plurality of conditions. The calibration processing is carried out by the processing unit 214 before the training process is started. The processing unit 214 stores, in the memory 22, various types of parameters determined through the calibration processing.

The input unit 215 accepts, from the operating unit 24, a designation signal designating one or more sets of electroencephalogram information for use in the calibration processing, from among multiple sets of electroencephalogram information acquired by the acquisition unit 211. That is to say, the memory 22 may store multiple sets of electroencephalogram information acquired by the acquisition unit 211. In the calibration processing, one or more sets of electroencephalogram information, designated by the designation signal, is used selectively from among those multiple sets of electroencephalogram information. In other words, the designation signal that the input unit 215 accepts from the operating unit 24 is a signal for designating the one or more sets of electroencephalogram information for use in the calibration processing, from among the multiple sets of electroencephalogram information stored in the memory 22.

3.2 Calibration Processing

Next, the operation of the electroencephalogram decision system 10 at the time of the calibration processing to be performed during the preparation process before the training process will be described in detail.

3.2.1 Overview of the Processing

The calibration processing is performed when the operation mode of the rehabilitation support system 100 is a calibration mode. The calibration processing is processing for determining various types of parameters including at least the threshold value corresponding to the activation level. In this embodiment, the calibration processing includes selection processing for selecting a decision condition from a plurality of conditions and a threshold value is determined with respect to the activation level depending on the decision condition. That is to say, the frequency band in which the power declines due to the event-related desynchronization and the magnitude of the decline in the power vary according to the attributes of the subject 5 (such as his or her age and sex), the affected region, the affected condition, and individual differences as described above. Thus, to improve the detection accuracy (decision accuracy) of the electroencephalogram to be detected, the electroencephalogram decision system 10 determines, through the calibration processing, various types of parameters for use to analyze the decision condition and the electroencephalogram information for individual subjects 5.

The calibration processing includes: measurement processing for making the electroencephalogram decision system 10 actually measure the subject's 5 electroencephalogram in the same procedure as in the training process; and calculation processing for determining various types of parameters according to this particular subject 5 based on the electroencephalogram measured. In addition, the calibration processing includes the selection processing as described above.

In the measurement processing, a calibration period, which is divided into the rest period and the exercise period as in the training period, is set, and the electroencephalogram is measured by the electroencephalogram decision system 10 during this calibration period. In each of the rest period and exercise period of the calibration period, the subject 5 undergoes his or her rehabilitation in accordance with the instructions given by the rehabilitation support system 100. In this embodiment, the calibration period may be 10 seconds, for example, and if the calibration period is evenly divided into two, then the first half of 5 seconds is supposed to be the "rest period" and the second half of 5 seconds is supposed to be the "exercise period."

In the rest period, the subject 5 puts his or her body at rest (i.e., does not plan to do (or imagine doing) the voluntary movement) to keep relaxed. On the other hand, in the exercise period, the subject 5 plans to do (or imagines doing) the action of stretching his or her hand fingers 53 as a voluntary movement. In both of the rest and exercise periods, the electroencephalogram decision system 10 measures the electroencephalogram specific to the subject 5. Also, the electroencephalogram decision system 10 has the electroencephalogram information, measured during the calibration period (including the rest period and the exercise period), stored as a record in the memory 22. As used herein, the "record" refers to the time-series data of the electroencephalogram information measured by the electroencephalogram decision system 10 since the beginning through the end of the calibration period during the measurement processing. Nevertheless, during the calibration period of the measurement processing, the electroencephalogram decision system 10 does not perform the processing of detecting a characteristic variation in the electroencephalogram unlike during the training period.

In this case, the electroencephalogram decision system 10 may perform the measurement processing a number of times during the calibration processing. The memory 22 may store a plurality of records as long as the number of records stored is equal to or less than a predetermined upper limit (of 30, for example). Thus, at the end point of the measurement processing that has been performed either once or a number of times, a single or a plurality of records, representing the subject's 5 electroencephalogram during the rest period and the exercise period, are stored in the memory 22.

The selection processing includes selecting, based on the electroencephalogram information acquired by the acquisition unit 211, a decision condition from a plurality of conditions (namely, first to fourth detection conditions). Next, an exemplary flow of the selection processing will be described with reference to the flowchart shown in FIG. 6. Note that the flowchart shown in FIG. 6 is an exemplary one. For example, Step S12 may be performed before, or in parallel with, Step S11. In addition, Steps S13, S14, and S17 may also be performed in an interchanged order.

In the selection processing, first of all, electroencephalogram information is acquired (in Step S10). More specifically, one or more records stored in the memory 22 are acquired by performing the measurement processing either once or a number of times. Next, an α-wave change rate and a β-wave change rate are calculated in Steps S11 and S12, respectively.

Step S11 includes calculating the α-wave change rate (i.e., a rate of change of a component falling within the first frequency band) based on the power on the frequency band basis analyzed by the analysis unit 212. For example, the analysis unit 212 calculates the power in the rest period and the power in the exercise period for each of a plurality of ranges included in the α-wave frequency band (e.g., a range from 8 Hz to less than 13 Hz). In this case, the plurality of ranges are frequency ranges defined by subdividing the α-wave frequency band. The plurality of ranges may include a number of 2 [Hz] ranges centered around 8 +n [Hz], where n is a value falling within the range from 1 to 3. The processing unit 214 calculates the α-wave change rate based on the respective powers in the rest and exercise periods with respect to each of the plurality of ranges. The α-wave change rate may be given, for example, by (Pa2−Pa1)/Pa1× 100 [%], where Pa1 indicates the power in the rest period and Pa2 indicates the power in the exercise period. One of the α-wave change rates thus calculated with respect to the plurality of ranges which has the largest absolute value is used to determine the decision condition. In addition, one of the plurality of ranges which has an α-wave change rate with the largest absolute value is selected as an α-wave frequency band for the subject 5.

Step S12 includes calculating the β-wave change rate (i.e., a rate of change of a component falling within the second frequency band) based on the power on the frequency band basis analyzed by the analysis unit 212. For example, the analysis unit 212 calculates the power in the rest period and the power in the exercise period for each of a plurality of ranges included in the β-wave frequency band (e.g., a range from 13 Hz to less than 30 Hz). In this case, the plurality of ranges are frequency ranges defined by subdividing the β-wave frequency band. The plurality of ranges may include a number of 2 [Hz] ranges centered around 13+m [Hz], where m is a value falling within the range from 1 to 15. The processing unit 214 calculates the β-wave change rate based on the respective powers in the rest and exercise periods with respect to each of the plurality of ranges. The β-wave change rate may be given, for example, by (Pb2−Pb1)/Pb1× 100 [%], where Pb1 indicates the power in the rest period and Pb2 indicates the power in the exercise period. One of the β-wave change rates thus calculated with respect to the plurality of ranges which has the largest absolute value is used to determine the decision condition. In addition, one of the plurality of ranges which has a β-wave change rate with the largest absolute value is selected as a β-wave frequency band for the subject 5.

When calculation of the α-wave change rate (in Step S11) and calculation of the β-wave change rate (in Step S12) are done, a decision is made whether or not the α-wave change rate is less than −5% (in Step S13). If the α-wave change rate is less than −5% (if the answer is YES in Step S13), the process proceeds to Step S14. On the other hand, if the α-wave change rate is equal to or greater than −5% (if the answer is NO in Step S13), the process proceeds to Step S15. In this case, the value of −5% is a value for determining whether or not there is any significant change in the α-wave frequency band (hereinafter referred to as an "α-wave decision value"). Note that the α-wave decision value does not have to be −5% but may be changed as appropriate.

In each of Steps S14 and S15, a decision is made whether or not the β-wave change rate is less than −5%. If the β-wave change rate is less than −5% in Step S14 (if the answer is YES in Step S14), the process proceeds to Step S16. On the other hand, if the β-wave change rate is equal to or greater than −5% (if the answer is NO in Step S14), the process proceeds to Step S17. Meanwhile, if the β-wave change rate is less than −5% in Step S15 (if the answer is YES in Step S15), the process proceeds to Step S18. On the other hand, if the β-wave change rate is equal to or greater than −5% (if the answer is NO in Step S15), the process proceeds to Step S19. In Steps S14 and S15, the value of −5% is a value for determining whether or not there is any significant change in the β-wave frequency band (hereinafter referred to as a "β-wave decision value"). Note that the β-wave decision value does not have to be −5% but may be changed as appropriate.

In Step S16, the first detection condition is selected as the decision condition. That is to say, the condition specifying the use of both of the α and β waves is selected. This condition is selected because a significant change has been detected in both of the α-wave frequency band and the β-wave frequency band. In Step S17, the second detection condition is selected as the decision condition. That is to say, a condition specifying the use of only the α wave out of the two is selected. This condition is selected because a significant change has been detected in only the α-wave frequency band. In Step S18, the third detection condition is selected as the decision condition. That is to say, a condition specifying the use of only the β wave out of the two is selected. This condition is selected because a significant change has been detected in only the β-wave frequency band. In Step S19, the fourth detection condition is selected as the decision condition. That is to say, a default condition is selected which specifies that a frequency band should be selected based on a healthy person's electroencephalogram irrespective of the subject's 5 electroencephalogram. This condition is selected because no significant change has been detected in the α-wave frequency band or the β-wave frequency band according to the subject's 5 electroencephalogram information.

As can be seen, the selection processing includes selecting, as the decision condition, one of the plurality of conditions (i.e., the first to fourth detection conditions) which is most suitable to the subject 5 based on the electroencephalogram information acquired by the acquisition unit 211.

The calculation processing includes determining various types of parameters on an individual subject 5 basis using the single or plurality of records stored in the memory 22 during the measurement processing that has been performed either once or a number of times. Specifically, the electroencephalogram decision system 10 makes the analysis unit 212 analyze, as needed, the electroencephalogram information acquired by the analysis unit 212 to determine various types of parameters based on the power analyzed on a frequency band basis by the analysis unit 212. The parameters to be determined at this time include at least a threshold value with respect to the activation level and the respective frequency bands of the α and β waves.

Next, it will be described briefly with reference to FIGS. 4, 5A, 5B, and 7 how to determine a threshold value with respect to a given activation level.

FIG. 4 is a graph plotting respective powers in the rest period and the exercise period in a situation where attention is paid to two frequency bands of the α and β waves (i.e., when the first detection condition is selected as the decision condition) with respect to a plurality of (e.g., five in this example) records. In FIG. 4, the abscissa indicates the power of the α wave, the ordinate indicates the power of the β wave, representative values (such as average values) of the power during the rest period are indicated by open circles (O), and representative values (such as average values) of the power during the exercise period are indicated by crosses (X). In FIG. 4, the respective frequency bands of the α and β waves are supposed to have already been determined with respect to the subject 5.

That is to say, in FIG. 4, with respect to the two frequency bands of the α and β waves, the range with the open circles (O) corresponds to the rest range A1 and the range with the crosses (X) corresponds to the exercise range A2. As described above, the electroencephalogram decision system 10 determines, when finding that the power falling within the particular frequency band has made a transition from the rest range to the exercise range, that an electroencephalogram with a characteristic variation that may arise when the subject 5 plans to do the voluntary movement should have been produced. Thus, the border line (i.e., the line Lth1) between the rest range A1 and the exercise range A2 in FIG. 4 corresponds to the threshold value with respect to the activation level.

FIG. 5A is a real number line plotting respective powers in the rest period and the exercise period in a situation where attention is paid to the α-wave frequency band (i.e., when the second detection condition is selected as the decision condition) with respect to a plurality of (e.g., four in this example) records. In FIG. 5A, representative values (such as average values) of the power during the rest period are indicated by open circles (O), and representative values (such as average values) of the power during the exercise period are indicated by crosses (X). In FIG. 5A, the frequency band of the α wave is supposed to have already been determined with respect to the subject 5. That is to say, in the α-wave frequency band shown in FIG. 5A, a range with the open circles (O) corresponds to the rest range A1, and a range with the crosses (X) corresponds to the exercise range A2. Therefore, in FIG. 5A, the border (the point Th1) between the rest range A1 and the exercise range A2 corresponds to a threshold value with respect to the activation level.

FIG. 5B is a real number line plotting respective powers in the rest period and the exercise period in a situation where attention is paid to the β-wave frequency band (i.e., when the third detection condition is selected as the decision condition) with respect to a plurality of (e.g., four in this example) records. In FIG. 5B, representative values (such as average values) of the power during the rest period are indicated by open circles (O), and representative values (such as average values) of the power during the exercise period are indicated by crosses (X). In FIG. 5B, the frequency band of the β wave is supposed to have already been determined with respect to the subject 5. That is to say, in the β-wave frequency band shown in FIG. 5B, a range with the open circles (O) corresponds to the rest range A1, and a range with the crosses (X) corresponds to the exercise range A2. Therefore, in FIG. 5B, the border (the point Th2) between the rest range A1 and the exercise range A2 corresponds to a threshold value with respect to the activation level.

As can be seen, the threshold value with respect to the activation level may be determined based on a single or a plurality of records obtained during the measurement processing.

The various types of parameters determined through the calibration processing are stored in the memory 22. In the training process to be performed later, the rehabilitation support system 100 will use the various types of parameters determined through the calibration processing.

Note that the threshold value does not have to be determined by the method described above, but may also be determined by any of various other methods such as linear discriminant analysis (LDA) and support vector machine (SVM).

Figure 7:
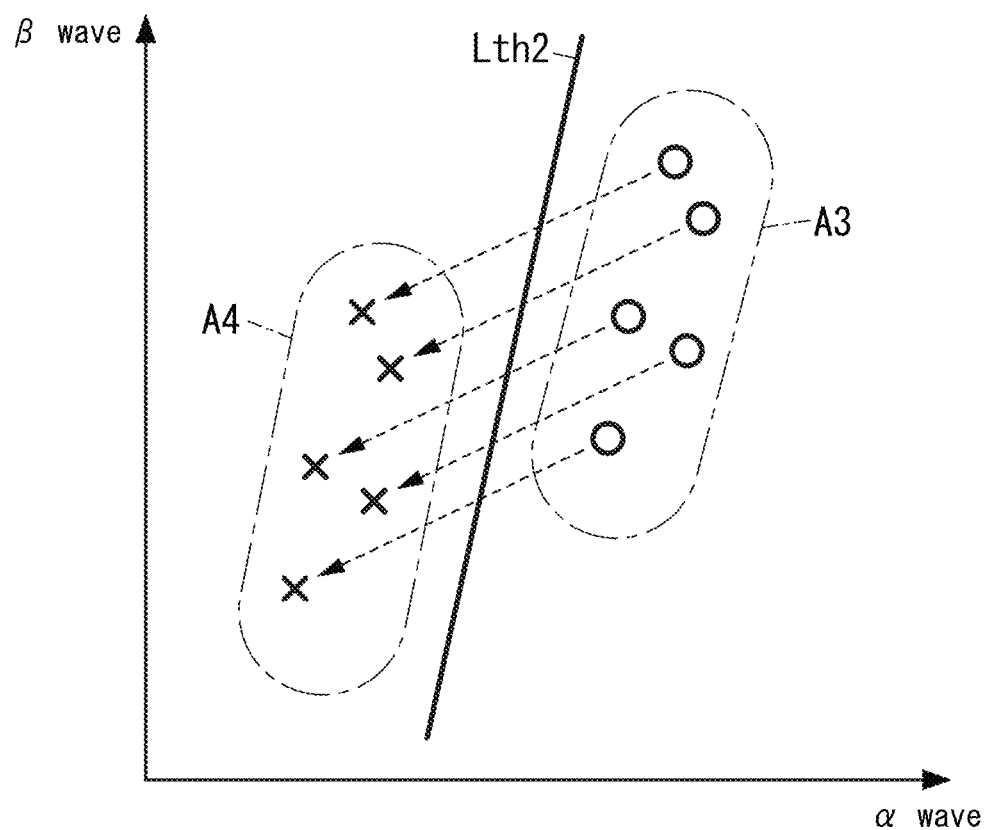
FIG. 7 is a graph showing how to determine a threshold value with respect to an activation level of the electroencephalogram decision system.

FIG. 7 is a graph plotting respective powers in the rest period and the exercise period in a situation where attention is paid to two frequency bands of the α and β waves (i.e., when the first detection condition is selected as the decision condition) with respect to a plurality of (e.g., five in this example) records as in FIG. 4. In FIG. 7, the abscissa indicates the power of the a wave, the ordinate indicates the power of the β wave, representative values (such as average values) of the power during the rest period are indicated by open circles (O), and representative values (such as average values) of the power during the exercise period are indicated by crosses (X). In FIG. 7, the respective frequency bands of the α and β waves are supposed to have already been determined with respect to the subject 5.

In FIG. 7, with respect to the two frequency bands of the α and β waves, the range with the open circles (O) corresponds to the rest range A3 and the range with the crosses (X) corresponds to the exercise range A4. As described above, the electroencephalogram decision system 10 determines, when finding that the power falling within the particular frequency band has made a transition from the rest range to the exercise range, that an electroencephalogram with a characteristic variation that may arise when the subject 5 plans to do the voluntary movement should have been produced. Thus, the border line (i.e., the line Lth2) between the rest range A3 and the exercise range A4 in FIG. 7 corresponds to the threshold value with respect to the activation level.

In a situation where calibration is carried out, the gradient of the border line between the rest range and the exercise range may go either zero or positive depending on the distribution of records (indicated by the open circles (O) and the crosses (X)) for calibration. FIG. 7 illustrates a situation where the gradient of the border line has gone positive. If the α-wave and β-wave power plots have made a transition from the rest range A3 to the exercise range A4, the α-wave power and the β-wave power causes a decline. Meanwhile, it has been confirmed that the chances of detecting movement intention increase when the α-wave power decreases and the β-wave power increases (see FIG. 4). Considering these respects, if the gradient of the border line is not negative but has gone zero or positive, then some reference may have been set against the event-related desynchronization (ERD) phenomenon related to the expression of the movement intention. Therefore, if the gradient of the border line is either zero or positive, a general border line (representing a default condition) as observed in a healthy person is suitably set.

In view of these considerations, the processing unit 214 may perform the selection processing for selecting a decision condition from a plurality of conditions based on components falling within the first and second (mutually different) frequency bands included in the electroencephalogram information acquired by the acquisition unit 211. In particular, the processing unit 214 may perform the selection processing for selecting the decision condition from the plurality of conditions based on a gradient of the border line between the rest range and the exercise range about the components falling within the first and second frequency bands. More specifically, when the gradient of the border line is negative (see the border line Lth1 shown in FIG. 4), the processing unit 214 may select the first detection condition. On the other hand, when the gradient of the border line is zero or positive (see the border line Lth2 shown in FIG. 7), the processing unit 214 may select the third type of condition (fourth detection condition).

3.2.2 Description of Screens

Next, the screens to be displayed on the display unit 26 of the information processor 2 during the calibration processing will be described with reference to FIGS. 8-10. Note that in the examples illustrated in FIGS. 8-10, the one-dot chain indicating the region and the reference signs are just shown there for the sake of convenience and are actually not displayed on the display unit 26.

Figure 8:
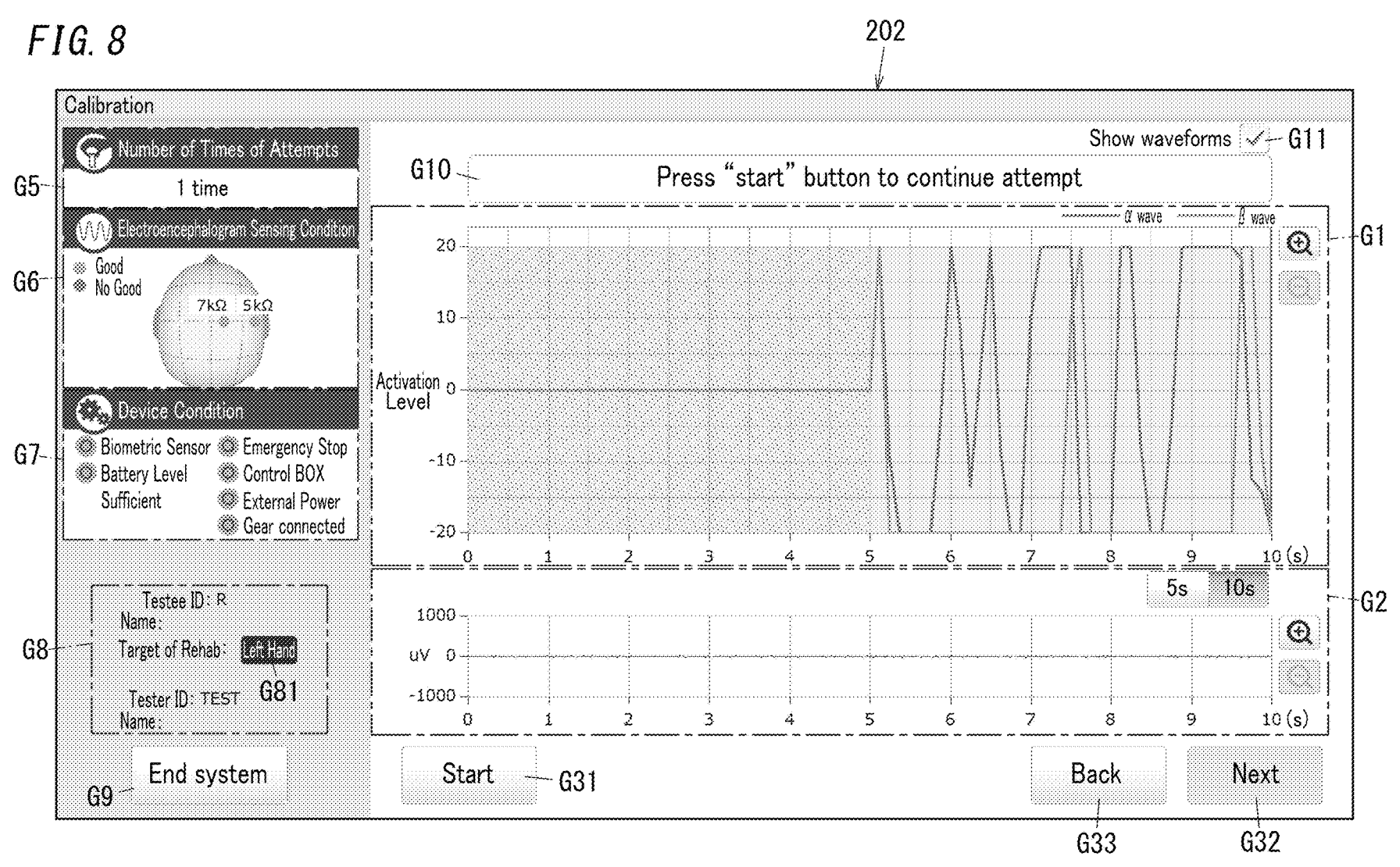

Specifically, first, during the measurement processing of the calibration processing, a calibration screen 202 such as the one shown in FIG. 8, for example, is displayed on the display unit 26 of the information processor 2. When the measurement processing ends, a selection screen 203 such as the one shown in FIG. 9 is displayed on the display unit 26 of the information processor 2. On the selection screen 203, a record for use in the calculation processing is selected. When the calculation processing ends, a calibration result screen 204 such as the one shown in FIG. 10 is displayed on the display unit 26 of the information processor 2.

As shown in FIG. 8, the calibration screen 202, as well as the training screen 200, also includes the activation level display area G1, the electroencephalogram display area G2, the number of times display area G5, the sensing condition display area G6, the device condition display area G7, the status display area G8, and the end button G9. The calibration screen 202 further includes not only the operation guidance area G10 and the checkbox G11 similar to their counterparts of the training screen 200, but also a start measurement button G31, a next button G32, and a back button G33 as well. The activation level display area G1 of the calibration screen 202 is basically the same as its counterpart of the training screen 200, but is different from the counterpart of the training screen 200 in that respective graphs of the α and β waves are displayed in the activation level display area G1. Likewise, the number of times display area G5 of the calibration screen 202 is basically the same as its counterpart of the training screen 200, but is different from the counterpart of the training screen 200 in that the "number of times of successes" is not displayed there.

In the activation level display area G1 of the calibration screen 202, a graph representing the activation level for the α wave (hereinafter referred to as an "α wave graph") and a graph representing the activation level for the β wave (hereinafter referred to as a "β wave graph") are displayed simultaneously. Nevertheless, the α wave graph and the β wave graph are displayed in mutually different modes (e.g., in two different colors) so as to be easily distinguished from each other. In addition, in the calibration processing, the threshold value with respect to the activation level has not been set yet. Thus, in the activation level display area G1, the line L1 indicating the threshold value (setting) is not displayed and no decision marks M1 are displayed, either, over the graph indicating the activation level. The activation level graph suitably has two different background colors for the rest period (i.e., the period of 0 to 5 seconds) defining the first half of the calibration period and the exercise period (i.e., the period of 5 to 10 seconds) defining the second half of the calibration period.

The start measurement button G31 is a button for starting the measurement processing. Tapping the start measurement button G31 causes the electroencephalogram decision system 10 to start measuring an electroencephalogram.

The next button G32 is a button for making a transition to the calculation processing. Tapping the next button G32 causes the electroencephalogram decision system 10 to end the measurement processing, thus changing the screens displayed on the display unit 26 of the information processor 2 from the calibration screen 202 to the selection screen 203 (see FIG. 9).

The back button G33 is a button for having the electroencephalogram decision system 10 go back to the state before the calibration processing is started. Tapping the back button G33 causes the electroencephalogram decision system 10 to end the calibration processing and go back to the state before the calibration processing is started.

Figure 9:
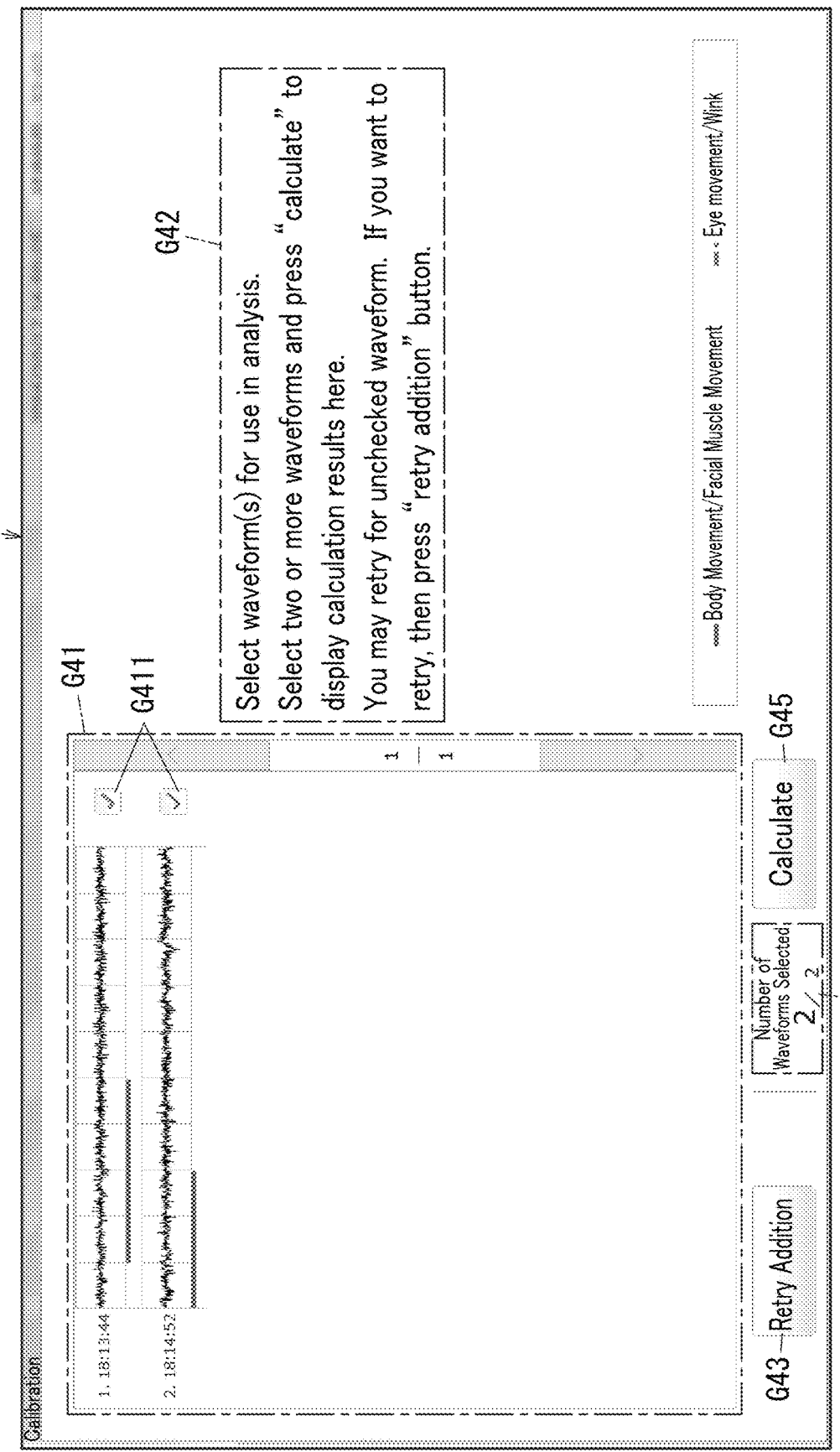
FIG. 9 illustrates an exemplary selection screen of the electroencephalogram decision system.

The selection screen 203 includes a record display area G41, an operation guidance area G42, a retry addition button G43, a selected records number display area G44, and a calculate button G45 as shown in FIG. 9.

The record display area G41 is an area for displaying the electroencephalograms that are stored as records in the memory 22. In this case, in the electroencephalogram graphs displayed in the record display area G41, as well as in the electroencephalogram display area G2, waveforms representing variations in electroencephalogram with time are displayed with the abscissa indicating the time (in seconds) and the ordinate indicating the potential. In the example illustrated in FIG. 9, with respect to a plurality of (e.g., two in this example) records stored in the memory 22, electroencephalograms are displayed one on top of another. In addition, in the record display area G41, checkboxes G411 are also displayed on the right of the respective electroencephalograms in association with the respective records. The checkboxes G411 are icons for selecting a record for use in the calculation processing. Tapping any of these checkboxes G411 alternately switches the state where its associated record is used for the calculation processing to the state where the associated record is not used for the calculation processing, and vice versa. When any of these checkboxes G411 is active on the screen, its associated record is used for the calculation processing.

In this case, if there are too many records to be displayed as a list in the record display area G41, then the records to be displayed in the record display area G41 may be scrolled up and down. This allows a lot of records, of which the number is even greater than that of the records displayable as a list in the record display area G41, to be displayed in the record display area G41.

At this time, the input unit 215 accepts, from the operating unit 24, a designation signal indicating a record selected by either the subject 5 or the medical staff by checking off any of the checkboxes G411. That is to say, when either the subject 5 or the medical staff selects a record for use in the calculation processing by checking off any of the checkboxes G411, one or more sets of electroencephalogram information for use in the calibration processing (calculation processing) is designated from among multiple sets of electroencephalogram information acquired by the acquisition unit 211.

The operation guidance area G42 is an area for displaying text information providing some guidance to operate the electroencephalogram decision system 10 properly. In the example illustrated in FIG. 9, displayed is text information saying "Select waveform(s) for use in analysis. Select two or more waveforms and press "calculate" to display calculation results here. You may retry for unchecked waveform. If you want to retry, then press "retry addition" button." The message displayed in the operation guidance area G42 varies according to the operating condition of the electroencephalogram decision system 10.

The retry addition button G43 is a button for starting an addition retry. As used herein, the "addition retry" refers to the processing of adding a record by performing the measurement processing all over again. Tapping the retry addition button G43 causes a transition to be made from the selection screen 203 to the calibration screen 202.

The selected records number display area G44 is an area for displaying the number of records (or waveforms) selected on the selection screen 203. Specifically, the number of records is shown as a fraction, which is the ratio of the number of records selected for use in the calculation processing (as the numerator) to the number of records displayed on the record display area G41 (i.e., the number of records stored in the memory 22) (as the denominator). For example, if the two records displayed in the record display area G41 are both selected (i.e., if the checkboxes G411 are both checked off) as shown in FIG. 9, then "2/2" is shown in the selected records number display area G44.

The calculate button G45 is a button for starting the calculation processing. Tapping the calculate button G45 causes the electroencephalogram decision system 10 to start the calculation processing using the records selected at that time on the selection screen 203.

Figure 10:
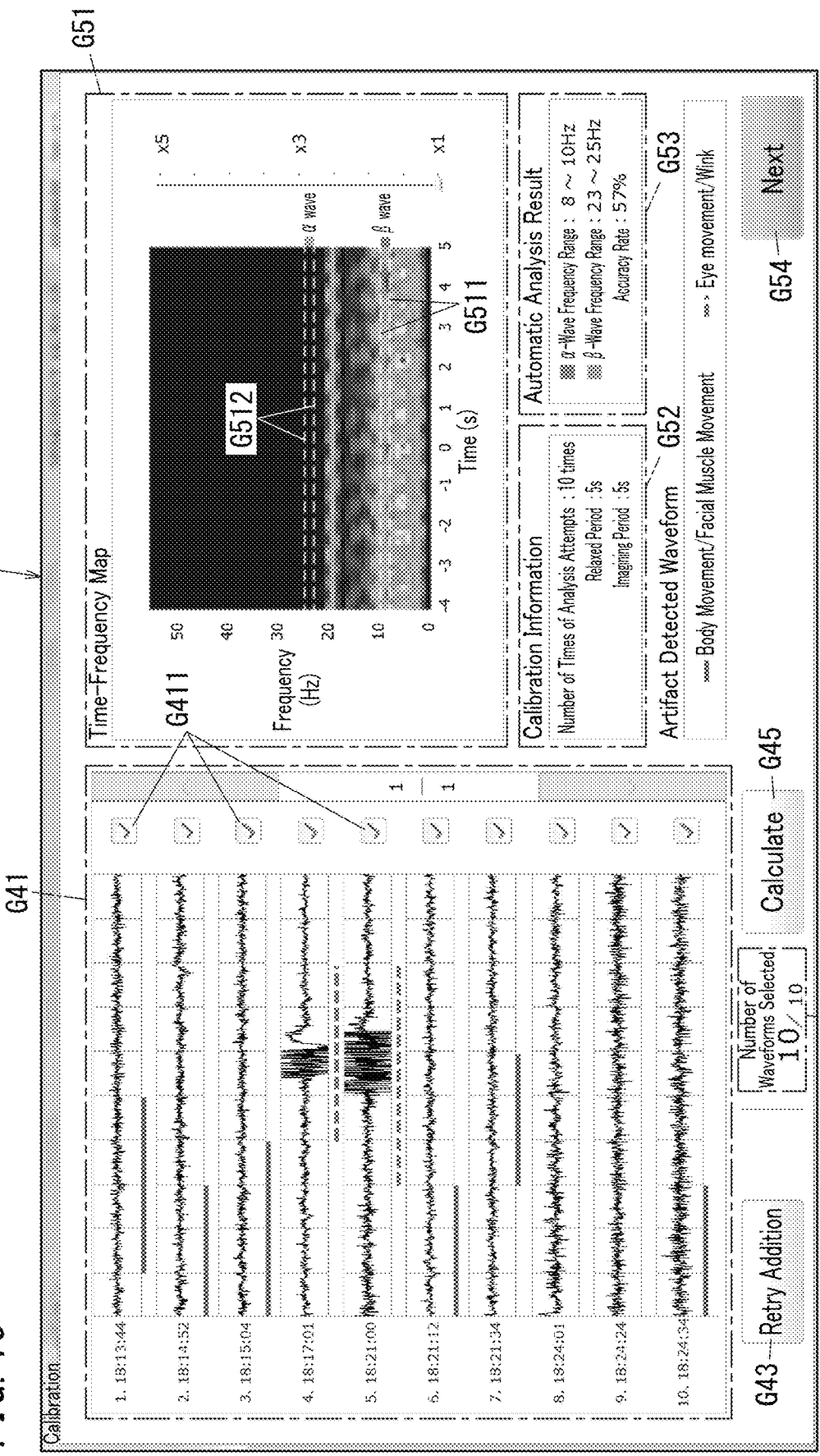
FIG. 10 illustrates an exemplary calibration result screen of the electroencephalogram decision system.

The calibration result screen 204, as well as the selection screen 203, includes the record display area G41, the retry addition button G43, the selected records number display area G44, and the calculate button G45 as shown in FIG. 10. In addition, the calibration result screen 204 further includes a time-frequency map G51, an information display area G52, an analysis result display area G53, and an end button G54.

The time-frequency map G51 is a graph showing the trend of a power variation in a particular frequency band during the calibration period used in the calculation processing. The time-frequency map G51 is a two-dimensional map, of which the abscissa indicates the time and the ordinate indicates the frequency and in which the power at each coordinate position is expressed by "color." For example, a color representing the power at each coordinate position is allocated in advance to each power range. For example, colors may be allocated to the respective power ranges such that the higher the power is, the brighter the color becomes. That is to say, the time-frequency map G51 visually displays the frequency band in which the power varies in a transition period from the rest period to the exercise period. In addition, in the time-frequency map G51, also displayed are lines G511 indicating the frequency band of the a wave calculated through the calculation processing and lines G512 indicating the frequency band of the β wave calculated through the calculation processing. Specifically, the lines G511 indicate the lower and upper limit values of the frequency band (or range) of the α wave, and the lines G512 indicate the lower and upper limit values of the frequency band (or range) of the β wave.

The information display area G52 is an area for displaying information about the measurement processing. In the example illustrated in FIG. 10, pieces of text information, indicating the number of times the measurement processing has been performed (i.e., the number of analysis attempts), the time length of the rest period (relaxed period), and the time length of the exercise period (imagining period), are displayed in the information display area G52.

The analysis result display area G53 is an area for displaying the results of analysis obtained through the calculation processing. In the example illustrated in FIG. 10, pieces of text information indicating the frequency band of the α wave (α wave frequency range), the frequency band of the β wave (β wave frequency range), and the ratio at which an electroencephalogram with the characteristic variation has been produced due to the event-related desynchronization (accuracy rate) are displayed in the analysis result display area G53.

The end button G54 is a button for ending the calibration processing. Tapping the end button G54 causes the electroencephalogram decision system 10 to end the calibration processing.

3.3 Training Process

Next, it will be described in detail how the electroencephalogram decision system 10 operates during the training process.

Figure 11:
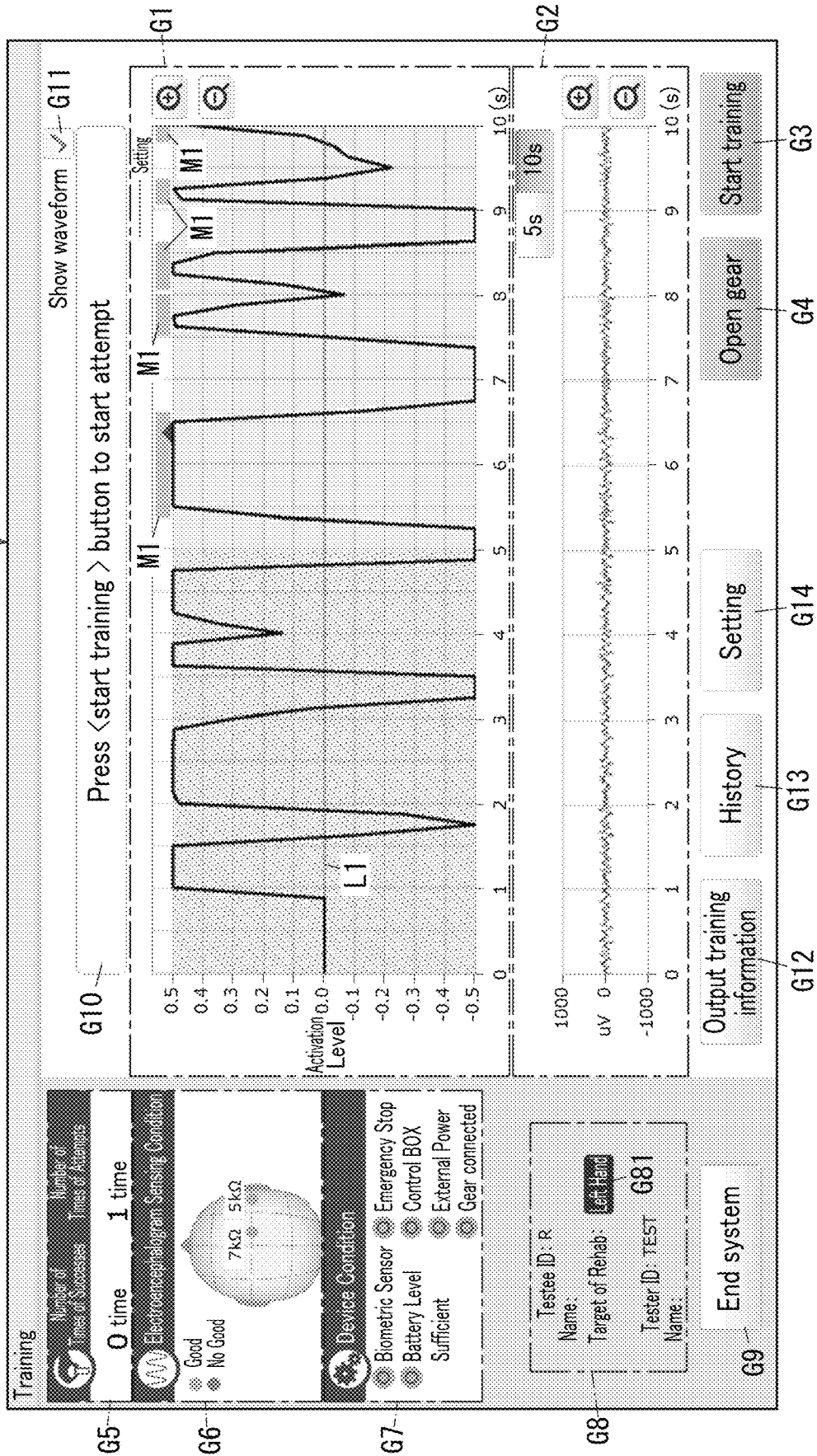
FIG. 11 illustrates an exemplary training screen of the electroencephalogram decision system.

During the training process, the operation mode of the rehabilitation support system 100 is a training mode. When the operation mode of the rehabilitation support system 100 is the training mode, a training screen 200 such as the one shown in FIG. 11 is displayed on the display unit 26 of the information processor 2. Note that in the example illustrated in FIG. 11, the one-dot chain indicating the region and the reference signs are just shown there for the sake of convenience and are actually not displayed on the display unit 26.

The training screen 200 includes an activation level display area G1, an electroencephalogram display area G2, a start training button G3, a gear operating button G4, a number of times display area G5, a sensing condition display area G6, a device condition display area G7, a status display area G8, and an end button G9. The training screen 200 further includes an operation guidance area G10, a checkbox G11, an output training information button G12, a history button G13, and a setting button G14.

The activation level display area G1 is an area for displaying an activation level graph. The activation level graph, of which the abscissa indicates the time (in seconds) and the ordinate indicates the activation level, displays a waveform showing how the activation level changes with time. In the activation level display area G1, the line L1 indicates a threshold value (as a setting). Also, in a period during which the activation level is greater than the threshold value, a decision mark M1 in the shape of a band is displayed over the activation level graph. In addition, the activation level graph suitably has two different background colors for the rest period (i.e., a period from 0 to 5 seconds) defining the first half of the training period and the exercise period (i.e., a period from 5 to 10 seconds) defining the second half of the training period, respectively.

The electroencephalogram display area G2 is an area for displaying the electroencephalogram measured by the headset 1. The electroencephalogram is displayed in the electroencephalogram display area G2 in real time in accordance with the electroencephalogram information transmitted from the headset 1 to the information processor 2. The electroencephalogram graph, of which the abscissa indicates the time (in seconds) and the ordinate indicates the potential, displays a waveform indicating how the electroencephalogram changes with time.

The start training button G3 is a button to be tapped to get the training started. Tapping the start training button G3 causes the training by the rehabilitation support system 100 to be started and also causes the electroencephalogram decision system 10 to start measuring the electroencephalogram.

The gear operating button G4 is a button allowing the subject 5 to operate the exercise assisting device 3. Tapping the gear operating button G4 causes the electroencephalogram decision system 10 to output a control signal to have the operation of closing or opening the exercise assisting device 3 performed. In this example, text information such as "close gear" or "open gear" is displayed on the gear operating button G4. Tapping the gear operating button G4 with "close gear" displayed causes the operation of closing the exercise assisting device 3 to be performed. Tapping the gear operating button G4 with "open gear" displayed causes the operation of opening the exercise assisting device 3 to be performed.

The number of times display area G5 is an area for displaying the number of times of successes and the number of times of attempts. As used herein, the "number of times of successes" indicates the number of times the electroencephalogram decision system 10 has successfully detected the electroencephalogram, having the characteristic variation that may arise due to event-related desynchronization when the subject 5 plans to do the voluntary movement, during the exercise period of the training period. Also, as used herein, the "number of times of attempts" indicates the number of times the training by the rehabilitation support system 100 has been carried out.

The sensing condition display area G6 is an area for displaying a specific condition in which the electroencephalogram is sensed. In this embodiment, the electroencephalogram decision system 10 measures the impedance value between the first electrode 111 and the subject's 5 body (i.e., his or her scalp) and the impedance value between the second electrode 112 and the subject's 5 body (i.e., his or her scalp), thereby determining, based on the impedance values measured, whether the electroencephalogram is sensed in good condition or not. In the example illustrated in FIG. 11, in the sensing condition display area G6, displayed are a text indicating the impedance values measured and markers indicating whether the electroencephalogram is sensed by each of the first electrode 111 and the second electrode 112 in good condition or not. Specifically, the markers on the illustration representing a human head change their colors depending on whether the electroencephalogram is sensed by each of the first electrode 111 and the second electrode 112 in good condition or not.

The device condition display area G7 is an area for displaying the respective conditions of various devices that form the rehabilitation support system 100. In the device condition display area G7, the condition of connection between the information processor 2 and the headset 1, the battery level of the headset 1, and other conditions are indicated by icons such as open circles (O) and crosses (X).

The status display area G8 is an area for displaying the identification information (testee ID) and name of the subject 5, and the identification information (tester ID) and name of the medical staff attending him or her. In addition, in the status display area G8, a target icon G81, indicating whether the "target of rehabilitation" is "left hand" or "right hand" is further displayed. In the example illustrated in FIG. 11, the target icon G81 indicates, as text information, that the target of rehabilitation is the "left hand."

The end button G9 is a button to be tapped to end the training. Tapping the end button G9 ends not only the training by the rehabilitation support system 100 but also the electroencephalogram measurement by the electroencephalogram decision system 10.

The operation guidance area G10 is an area for displaying text information providing guidance on how to operate the rehabilitation support system 100. In the example illustrated in FIG. 11, the text information that says "press <start training> button to start attempt" is displayed in the operation guidance area G10. The message displayed in the operation guidance area G10 varies according to the operating state of the rehabilitation support system 100.

The checkbox G11 is an icon for switching the state of displaying the electroencephalogram in the electroencephalogram display area G2 into the state of displaying no electroencephalograms there, and vice versa. Tapping the checkbox G11 causes the display state to be switched alternately from the state where the electroencephalogram is displayed in the electroencephalogram display area G2 to the state where the electroencephalogram is not displayed in the electroencephalogram display area G2, and vice versa. While the checkbox G11 is checked off, the electroencephalogram is displayed in the electroencephalogram display area G2.

The output training information button G12 is a button for outputting training information including the result of rehabilitation. Tapping the output training information button G12 causes the training information to be output in any desired form. For example, the training information may be output as a text message displayed, a verbal message emitted, a page printed out, a file written into a non-transitory storage medium, or data transmitted to a telecommunications device, for example.

The history button G13 is a button allowing the user to make reference to the history of the training information including the results of rehabilitation. Tapping the history button G13 changes the screens displayed on the display unit 26 of the information processor 2 from the training screen 200 to a history reference screen. On the history reference screen, at least the results of rehabilitations that the subject 5 has undergone so far are displayed.

The setting button G14 is a button for changing the operation mode of the rehabilitation support system 100 into the setting mode in which various types of settings are made about the rehabilitation support system 100. Tapping the setting button G14 changes the screens displayed on the display unit 26 of the information processor 2 from the training screen 20 to a setting screen.

During the training process, the subject 5 undergoes the rehabilitation with the training screen 200 described above displayed on the display unit 26 of the information processor 2. That is to say, tapping the start training button G3 causes the training by the rehabilitation support system 100 to be started.

As soon as the training is started, the training time starts being counted, and the electroencephalogram decision system 10 starts measuring the electroencephalogram specific to the subject 5. During the rest period (i.e., the period from 0 to 5 seconds) that is the first half of the training period, the subject 5 puts his or her body at rest in accordance with the guidance displayed in the operation guidance area G10 or the instruction given by the medical staff attending him or her. At this time, the activation level and the electroencephalogram are displayed in real time on the training screen 200. During the rest period, however, the electroencephalogram decision system 10 does not compare the activation level with the threshold value and does not detect an electroencephalogram with the characteristic variation caused by the event-related desynchronization, either.

On the other hand, during the exercise period (i.e., the period from 5 to 10 seconds) defining the second half of the training period, the subject 5 plans to do (or imagines doing) the action of stretching his or her hand fingers 53 as a voluntary movement in accordance with either the guidance displayed in the operation guidance area G10 or the instruction given by the medical staff attending him or her. At this time, the activation level and the electroencephalogram are displayed in real time on the training screen 200. In addition, during the exercise period, the electroencephalogram decision system 10 compares the activation level with the threshold value, thereby detecting an electroencephalogram with the characteristic variation caused by the event-related desynchronization. In this case, when the event-related desynchronization causes the activation level to exceed the threshold value (as indicated by the line L1 in FIG. 11), the band-shaped decision mark M1 appears over the activation level graph on the training screen 200.

Next, it will be described in further detail with reference to the flowchart shown in FIG. 12 how the electroencephalogram decision system 10 performs the decision processing. First, the acquisition unit 211 acquires electroencephalogram information from the headset 1 (in Step S20). Next, the detection unit 213 determines a decision condition (in Step S21) based on the result of the selection processing by the processing unit 214 and acquires a threshold value with respect to the decision condition (in Step S22). In this case, the electroencephalogram decision system 10 makes the analysis unit 212 analyze, as needed, the electroencephalogram information acquired by the acquisition unit 211. In Step S23 next to Step S22, the electroencephalogram decision system 10 makes the detection unit 213 calculate the activation level based on the power on the frequency band basis analyzed by the analysis unit 212 and compare the activation level with the threshold value. The electroencephalogram decision system 10 determines, when the event-related desynchronization causes a decline in the power in the particular frequency band to have the power in the particular frequency band make a transition from the rest range to the exercise range, that the activation level should have exceeded the threshold value.

In Step S23, the particular frequency band may be either a single frequency band (which may be, for example, either the α-wave band or the β-wave band) or plurality of frequency bands (which may be, for example, both the α-wave band the β-wave band) depending on the decision condition. If the particular frequency band includes two frequency bands as in the first detection condition and the fourth detection condition, a decision is made that the activation level should have exceeded the threshold value when the coordinate values defined by the powers of the two frequency bands make a transition from the rest range to the exercise range. On the other hand, if the particular frequency band is a single frequency band as in the second detection condition and the third detection condition, then a decision is made that the activation level should have exceeded the threshold value when the value defined by the power in the single frequency band makes a transition from the rest range to the exercise range.

When a decision is made that the activation level should be greater than the threshold value (if the answer is YES in Step S23), the detection unit 213 determines that the target electroencephalogram should have been produced (in Step S24). On the other hand, when a decision is made that the activation level should be equal to or less than the threshold value (if the answer is NO in Step S23), the detection unit 213 determines that the target electroencephalogram should not have been produced yet (in Step S25).

In addition, according to this embodiment, the electroencephalogram decision system 10 also has the capability of measuring the duration for which the activation level remains greater than the threshold value. In the training screen 200 illustrated as an example in FIG. 11, the length of each decision mark M1 corresponds to the length of the duration. When the activation level rises (i.e., changes) from a value equal to or less than the threshold value to a value greater than the threshold value, the electroencephalogram decision system 10 transmits the third control signal to the controller 4. Furthermore, when the duration reaches a prescribed amount of time (of 1 second, for example), the electroencephalogram decision system 10 transmits the first control signal to the controller 4.

As can be seen from the foregoing description, when the activation level exceeds the threshold value, the electrical stimulus generator 32 of the exercise assisting device 3 is driven and the exercise assisting device 3 applies an electrical stimulus to the subject's 5 body, thereby assisting the subject 5 with his or her voluntary movement (i.e., the stretching action in this case). Furthermore, when the activation level remains greater than the threshold value for the prescribed amount of time, the finger exerciser 31 of the exercise assisting device 3 is driven and the exercise assisting device 3 performs the "opening operation" with respect to the finger exerciser 31, thereby assisting the subject 5 with his or her voluntary movement (stretching action in this case).

As a result, in a situation where the subject 5 plans to do (or imagines doing) the voluntary movement, the exercise assisting device 3 assists the subject 5 with his or her voluntary movement (i.e., the action of stretching his or her left hand fingers 53) exactly at the timing when a brain region corresponding to the target region of the voluntary movement is actually activated. At this time, the subject's 5 muscle and sensory nerve start their activity and the information is transmitted to the brain, thereby reconstructing the nerve system and achieving some rehabilitation effect. This allows the rehabilitation support system 100 to support the subject 5 in his or her rehabilitation by exercise therapy as well as in a situation where medical staff assists subjects 5 in various conditions and more effectively than in a situation where the subject 5 does the voluntary movement by him- or herself.

Variations

The embodiment described above is only one of various embodiments of the present disclosure, and may be readily modified in various manners depending on a design choice or any other factor, without departing from the scope of the present disclosure. Also, the same function as that of the electroencephalogram decision system 10 may also be implemented as an electroencephalogram decision method, a (computer) program, or a non-transitory storage medium that stores the program thereon, for example. An electroencephalogram decision method according to an aspect includes a first step and a second step. The first step includes acquiring electroencephalogram information representing an electroencephalogram obtained by an electrode unit 11 placed on a region of interest 51 that forms part of a subject's 5 head 52. The second step includes making a decision, when finding the electroencephalogram information acquired in the first step satisfying a decision condition, that a target electroencephalogram, which is an electroencephalogram with a characteristic variation, should have been produced. The decision condition is selected from a plurality of conditions. The plurality of conditions includes a first type of condition and a second type of condition. The first type of condition specifies that a decision should be made, based on a component falling within a single frequency band included in the electroencephalogram represented by the electroencephalogram information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced. A (computer) program according to another aspect is designed to cause a computer system to carry out the electroencephalogram decision method described above.

Next, variations of the embodiment described above will be enumerated one after another. Note that any of the variations to be described below may be combined as appropriate.

The electroencephalogram decision system 10 according to the present disclosure includes a computer system. In that case, the computer system may include, as principal hardware components, a processor and a memory. The functions of the electroencephalogram decision system 10 according to the present disclosure may be performed by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be made up of a single or a plurality of electronic circuits including a semiconductor integrated circuit (IC) or a largescale integrated circuit (LSI). As used herein, the "integrated circuit" such as an IC or an LSI is called by a different name depending on the degree of integration thereof. Examples of the integrated circuits include a system LSI, a very largescale integrated circuit (VLSI), and an ultra largescale integrated circuit (ULSI). Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be integrated together in a single device or distributed in multiple devices without limitation.

Also, in the embodiment described above, the plurality of constituent elements of the information processor 2 are integrated together in a single housing. However, this is not a configuration essential to the electroencephalogram decision system 10. Alternatively, those constituent elements of the information processor 2 may be distributed in multiple different housings. Even when a plurality of constituent elements are distributed in multiple different housings, those constituent element are still able to serve as the electroencephalogram decision system 10 in conjunction with each other when connected together via a network such as the Internet. Still alternatively, at least some functions of the electroencephalogram decision system 10 may be implemented as a server or a cloud computing system as well. Conversely, the plurality of functions distributed in multiple devices such as the headset 1 and the information processor 2 may be integrated as parts of the electroencephalogram decision system 10, along with the other constituent elements of the electroencephalogram decision system 10, in a single housing.

Also, the electrode unit 11 does not have to be configured to come into contact with the surface of the subject's 5 head 52 (i.e., the scalp). Alternatively, the electrode unit 11 may also be configured to come into contact with the surface of the brain, for example.

Furthermore, the rehabilitation support system 100 does not always support the subject 5 in his or her rehabilitation to recover the proper function of his or her hand fingers but may also support the subject 5 in his or her rehabilitation for any other body region such as his or her shoulder(s), elbow(s), upper arm(s), waist, lower limbs, or upper limbs. The characteristic variation of an electroencephalogram that may arise when the subject 5 plans to do (or imagines doing) voluntary movement may vary depending on the target region of the rehabilitation or the type of the movement. For example, if an event-related synchronization (ERS) occurs when the subject 5 plans to do the voluntary movement, the power in a particular frequency band increases in the electroencephalogram representing a brain wave measured in the vicinity of the motor area during the voluntary movement. In that case, the electroencephalogram decision system 10 detects, by seeing the power increase in the particular frequency band, the characteristic variation in electroencephalogram. Also, the target electroencephalogram to be detected by the electroencephalogram decision system 10 does not have to be an electroencephalogram with a characteristic variation that may arise when the subject 5 plans to do voluntary movement. Alternatively, the target electroencephalogram to be detected may also be an electroencephalogram with a characteristic variation that may arise when the subject 5 is provided with a predetermined type of information. In this case, examples of the predetermined type of information include visual information (such as video and images) and auditory information (such as sounds or voices and music). That is to say, as long as the target electroencephalogram to be detected by the electroencephalogram decision system 10 is an electroencephalogram with some characteristic variation, its characteristic variation may be caused by any factor.

Also, the plurality of conditions to be decision conditions need to include at least one first type of condition and at least one second type of condition, and does not have to include a third type of condition. Furthermore, in the embodiment described above, a condition that uses two different frequency bands (hereinafter referred to as a "first frequency band" and a "second frequency band," respectively) as a second type of condition has been described as an example. However, this is only an example and should not be construed as limiting. Alternatively, the number of multiple different frequency bands may also be three or more. Furthermore, the combination of the first frequency band and the second frequency band does not have to be a combination of the α-wave frequency band and the β-wave frequency band. Rather, the combination of the frequency bands may be changed as appropriate according to the target electroencephalogram to be detected.

Furthermore, in the decision processing, the α-wave decision value and the β-wave decision value may be changed. For example, as the α-wave decision value and the β-wave decision value decrease, it becomes easier to select the fourth detection condition than the first detection condition. On the other hand, as the α-wave decision value and the β-wave decision value increase, it becomes easier to select the first detection condition than the fourth detection condition. Therefore, if a higher priority needs to be given to providing rehabilitation on the same standard as a healthy person, then the α-wave decision value and the β-wave decision value may be decreased. On the other hand, if a higher priority needs to be given to providing rehabilitation suited to the subject's 5 level, then the α-wave decision value and the β-wave decision value may be increased. The α-wave change rate and the β-wave change rate are both negative values in the embodiment described above, but may also be positive values. In that case, the α-wave decision value and the β-wave decision value may also be positive values.

Furthermore, the rehabilitation support system 100 does not have to be configured to apply either an electrical stimulus or a mechanical (or dynamic) stimulus to the subject 5 but may also be configured to apply a visual stimulus to the subject 5 by presenting virtual video to him or her. In that case, when the subject 5 plans to do the voluntary movement, the rehabilitation support system 100 presents virtual video, representing his or her affected region as if the affected region were functioning normally, to him or her exactly at the timing when his or her brain region corresponding to the target region of the voluntary movement is actually activated. This also allows the rehabilitation support system 100 to support the subject 5 in his or her voluntary movement.

Furthermore, the exercise assisting device 3 and the controller 4 do not have to be provided separately from each other. Alternatively, the exercise assisting device 3 and the controller 4 may also be housed and integrated together in the same housing.

Furthermore, the method of communication between the headset 1 and the information processor 2 is supposed to be wireless communication in the embodiment described above, but may also be wired communication or communications via a relay, for example. Furthermore, the method of communication between the controller 4 and the information processor 2 is supposed to be wired communication in the embodiment but may also be wireless communication or communication via a relay, for example.

Furthermore, the headset 1 does not have to be driven by a battery but the power to operate the signal processing unit 12, the first communications unit 13, and other components may also be supplied from the information processor 2, for example.

Furthermore, the information processor 2 does not have to be configured to acquire electroencephalogram information from the dedicated headset 1. Alternatively, the information processor 2 may also be configured to acquire electroencephalogram information from a general-purpose electroencephalograph, for example.

Resume

As can be seen from the foregoing description of embodiments and their variations, an electroencephalogram decision system (10) according to a first aspect includes an acquisition unit (211) and a detection unit (213). The acquisition unit (211) is configured to acquire electroencephalogram information representing an electroencephalogram obtained by an electrode unit (11) placed on a region of interest (51) that forms part of a subject's (5) head (52).

The detection unit (213) is configured to determine, when finding the electroencephalogram information acquired by the acquisition unit (211) satisfying a decision condition, that a target electroencephalogram, which is an electroencephalogram with a characteristic variation, should have been produced. The decision condition is selected from a plurality of conditions. The plurality of conditions includes a first type of condition and a second type of condition. The first type of condition specifies that a decision should be made, based on a component falling within a single frequency band included in the electroencephalogram represented by the electroencephalogram information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced. The first aspect improves the decision accuracy of electroencephalograms.

An electroencephalogram decision system (10) according to a second aspect, which may be realized in combination with the first aspect, further includes a processing unit (214) configured to perform selection processing for selecting, in accordance with the electroencephalogram information acquired by the acquisition unit (211), the decision condition from the plurality of conditions. The second aspect allows a decision condition suitable to each individual subject to be selected from a plurality of conditions.

In an electroencephalogram decision system (10) according to a third aspect, which may be realized in combination with the first or second aspect, the second type of condition includes a first detection condition specifying that the target electroencephalogram should be detected based on components falling within first and second frequency bands that are different from each other. The first type of condition includes: a second detection condition specifying that the target electroencephalogram should be detected based on a component falling within the first frequency band, not the second frequency band; and a third detection condition specifying that the target electroencephalogram should be detected based on a component falling within the second frequency band, not the first frequency band. The third aspect increases the chances of one of the plurality of conditions being a decision condition suitable to each individual subject.

In an electroencephalogram decision system (10) according to a fourth aspect, which may be realized in combination with the third aspect, the first frequency band is an α-wave frequency band, and the second frequency band is a β-wave frequency band. The fourth aspect improves the decision accuracy of an electroencephalogram with a characteristic variation that may arise when the subject (5) plans to do voluntary movement.

In an electroencephalogram decision system (10) according to a fifth aspect, which may be realized in combination with any one of the first to fourth aspects, the plurality of conditions further includes a third type of condition specifying that a decision should be made, based on a component falling within one or more frequency bands selected according to a healthy person's electroencephalogram, whether or not the target electroencephalogram has been produced. The fifth aspect improves the decision accuracy of electroencephalograms with a healthy person's electroencephalogram used as a reference.

In an electroencephalogram decision system (10) according to a sixth aspect, which may be realized in combination with the second aspect, the processing unit (214) is configured to perform the selection processing for selecting the decision condition from the plurality of conditions based on components falling within the first and second frequency bands included in the electroencephalogram information acquired by the acquisition unit (211). The first and second frequency bands are different from each other. The sixth aspect allows a decision condition suitable to each individual subject to be selected from a plurality of conditions.

In an electroencephalogram decision system (10) according to a seventh aspect, which may be realized in combination with the sixth aspect, the processing unit (214) is configured to perform the selection processing for selecting the decision condition from the plurality of conditions based on a gradient of a border line (Lth1, Lth2) between a rest range (A1, A3) and an exercise range (A2, A4) about the components falling within the first and second frequency bands. The seventh aspect allows a decision condition suitable to each individual subject to be selected from a plurality of conditions.

In an electroencephalogram decision system (10) according to an eighth aspect, which may be realized in combination with the seventh aspect, the rest range (A1, A3) is a range in which the components falling within the first and second frequency bands of the subject's (5) electroencephalogram are able to fall when the subject (5) puts his or her body at rest. The eighth aspect allows a decision condition suitable to each individual subject to be selected from a plurality of conditions.

In an electroencephalogram decision system (10) according to a ninth aspect, which may be realized in combination with the seventh or eighth aspect, the exercise range (A2, A4) is a range in which the components falling within the first and second frequency bands of the subject's (5) electroencephalogram are able to fall when the subject (5) plans to do voluntary movement. The ninth aspect allows a decision condition suitable to each individual subject to be selected from a plurality of conditions.

In an electroencephalogram decision system (10) according to a tenth aspect, which may be realized in combination with any one of the seventh to ninth aspects, the second type of condition includes a first detection condition specifying that the target electroencephalogram should be detected based on components falling within first and second frequency bands. The processing unit (214) is configured to, when finding the gradient of the border line (Lth1, Lth2) negative, select the first detection condition. The tenth aspect allows a decision condition suitable to each individual subject to be selected from a plurality of conditions.

In an electroencephalogram decision system (10) according to an eleventh aspect, which may be realized in combination with the tenth aspect, the detection unit (213) is configured to determine, by seeing the components falling within the first and second frequency bands make a transition from the rest range (A1, A3) to the exercise range (A2, A4), that the target electroencephalogram should have been produced according to the first detection condition. The eleventh aspect improves the decision accuracy of electroencephalograms.

In an electroencephalogram decision system (10) according to a twelfth aspect, which may be realized in combination with any one of the seventh to eleventh aspects, the plurality of conditions further includes a third type of condition specifying that a decision be made, based on a component falling within one or more frequency bands selected according to a healthy person's electroencephalogram, whether or not the target electroencephalogram has been produced. The processing unit (214) is configured to select the third type of condition when finding a gradient of the border line zero or positive. The twelfth aspect allows a decision condition suitable to each individual subject to be selected from a plurality of conditions.

An electroencephalogram decision method according to a thirteenth aspect includes a first step and a second step. The first step includes acquiring electroencephalogram information representing an electroencephalogram obtained by an electrode unit (11) placed on a region of interest (51) that forms part of a subject's (5) head (52). The second step includes making a decision, when finding the electroencephalogram information acquired in the first step satisfying a decision condition, that a target electroencephalogram, which is an electroencephalogram with a characteristic variation, should have been produced. The decision condition is selected from a plurality of conditions. The plurality of conditions includes a first type of condition and a second type of condition. The first type of condition specifies that a decision should be made, based on a component falling within a single frequency band included in the electroencephalogram represented by the electroencephalogram information, whether or not the target electroencephalogram has been produced. The second type of condition specifies that a decision should be made, based on components falling within multiple different frequency bands included in the electroencephalogram represented by the electroencephalogram information, whether or not the target electroencephalogram has been produced. The thirteenth aspect improves the decision accuracy of electroencephalograms.

A program according to a fourteenth aspect is designed to cause a computer system to carry out the electroencephalogram decision method of the thirteenth aspect. The fourteenth aspect improves the decision accuracy of electroencephalograms.

A non-transitory storage medium according to a fifteenth aspect is readable for a computer system and stores a program designed to cause the computer system to carry out the electroencephalogram decision method of the thirteenth aspect. The fifteenth aspect improves the decision accuracy of electroencephalograms.

A rehabilitation support system (100) according to a sixteenth aspect includes the electroencephalogram decision system (10) according to any one of the first to twelfth aspects, an exercise assisting device (3), and a controller (4). The exercise assisting device (3) has the capability of applying at least one of a mechanical stimulus or an electrical stimulus to the subject (5). The controller (4) is configured to control the exercise assisting device (3) when the detection unit (213) of the electroencephalogram decision system (10) determines that the target electroencephalogram should have been produced. The sixteenth aspect improves the decision accuracy of electroencephalograms.

Note that these aspects are only exemplary aspects of the present disclosure. Various configurations (including their variations) for the electroencephalogram decision system (10) according to the embodiment may also be implemented as an electroencephalogram decision method, a (computer) program, or a non-transitory storage medium on which the program is stored.

Also, the constituent elements according to the second to twelfth aspects are not essential constituent elements for the electroencephalogram decision system (10) but may be omitted as appropriate.

REFERENCE SIGNS LIST

10 Electroencephalogram Decision System
11 Electrode Unit
211 Acquisition Unit
213 Detection Unit
214 Processing Unit
5 Subject
51 Region of Interest
52 Head

The invention claimed is:

1. An electroencephalogram decision system comprising:
an acquisition unit configured to acquire electroencephalogram information, the electroencephalogram information representing an electroencephalogram obtained by an electrode unit, the electrode unit configured to be placed on a region of interest that forms part of a subject's head;
an analysis unit configured to calculate each of powers of first and second frequency bands included in a frequency spectrum of the electroencephalogram represented by the electroencephalogram information acquired by the acquisition unit, the first and second frequency bands being different from each other;
a detection unit configured to determine, based on a decision condition, whether or not the electroencephalogram information represents a target electroencephalogram which is an electroencephalogram with a characteristic variation;
a processing unit; and
at least one of (a) an exercise assisting device configured to support the subject in his or her voluntary movement by applying at least one of a mechanical stimulus or an electrical stimulus to the subject in coordination with the determination by the detection unit or (b) a display unit configured to display an image for guiding his or her voluntary movement based on the determination by the detection unit,
the decision condition being selected from a plurality of conditions,
the plurality of conditions including a first type of condition and a second type of condition,
the first type of condition determines that the acquired electroencephalogram information equals the target electroencephalogram when a power of a single one of the first and second frequency bands transitions from a rest range to an exercise range
the second type of condition determines that the acquired electroencephalogram information equals the target electroencephalogram when each of the powers of the first and second frequency bands transition from the rest range to the exercise range,
the processing unit being configured to select the decision condition from the plurality of conditions based on a rate of change of a border line between the rest range and the exercise range on a graph where one axis represents a power of the first frequency band and another one-axis represents a power of the second frequency band,
wherein, where the detection unit determines that the electroencephalogram information represents the target electroencephalogram, the at least one of the exercise assisting device or the display unit respectively supports the subject in his or her voluntary movement by applying the at least one of the mechanical stimulus or the electrical stimulus to the subject or displaying the image for guiding his or her voluntary movement.

2. The electroencephalogram decision system of claim 1, wherein
the first frequency band is an a-wave frequency band, and
the second frequency band is a B-wave frequency band.

3. The electroencephalogram decision system of claim 1, wherein
the plurality of conditions further includes a third type of condition specifying that a decision be made, based on a power of one or more frequency bands selected according to a healthy person's electroencephalogram, whether or not the electroencephalogram information represents the target electroencephalogram.

4. The electroencephalogram decision system of claim 1, wherein
the rest range is a range in which each of the powers of the first and second frequency bands of the acquired electroencephalogram are able to fall when the subject puts his or her body at rest.

5. The electroencephalogram decision system of claim 1, wherein
the exercise range is a range in which each of the powers of the first and second frequency bands of the acquired electroencephalogram are able to fall when the subject plans to do voluntary movement.

6. The electroencephalogram decision system of claim 1, wherein the processing unit is configured to, when finding the rate of change of the border line is negative, select the second type of condition.

7. The electroencephalogram decision system of claim 6, wherein
the detection unit is configured to determine, by seeing each of the powers of the first and second frequency bands make a transition from the rest range to the exercise range, that the electroencephalogram information represents the target electroencephalogram according to the second type of condition.

8. The electroencephalogram decision system of claim 1, wherein
the plurality of conditions further includes a third type of condition specifying that a decision be made, based on a power of one or more frequency bands selected according to a healthy person's electroencephalogram, whether or not the electroencephalogram information represents the target electroencephalogram, and the processing unit is configured to select the third type of condition when finding the rate of change of the border line is zero or positive.

9. The electroencephalogram decision system of claim 1, wherein the rate of change of the border line between the rest range and the exercise range on the graph where the one axis represents the power of the first frequency band and the another axis represents the power of the second frequency band corresponds to a slope of a decision boundary, calculated by linear discriminant analysis (LDA) method, between the rest range and the exercise range on the graph where the one axis represents the power of the first frequency band and the another one-axis represents the power of the second frequency band.

10. An electroencephalogram decision method comprising:
- a first step of acquiring electroencephalogram information, the electroencephalogram information representing an electroencephalogram obtained by an electrode unit, the electrode unit being placed on a region of interest that forms part of a subject's head;
- an analysis step of calculating each of powers of first and second frequency bands included in a frequency spectrum of the electroencephalogram represented by the electroencephalogram information acquired by the first step, the first and second frequency bands being different from each other;
- a second step of making a decision, based on a decision condition, whether or not the electroencephalogram information represents a target electroencephalogram which is an electroencephalogram with a characteristic variation; and
- at least one of (a) an exercise assisting step of supporting the subject in his or her voluntary movement by applying at least one of a mechanical stimulus or an electrical stimulus to the subject in coordination with the determination by the second step or (b) a displaying step of displaying an image for guiding his or her voluntary movement based on the determination by the second step,
- the decision condition being selected from a plurality of conditions,
- the plurality of conditions including a first type of condition and a second type of condition,
- the first type of condition determining that the acquired electroencephalogram information equals the target electroencephalogram when a power of a single one of the first and second frequency bands transitions from a rest range to an exercise range
- the second type of condition determining that the acquired electroencephalogram information equals the target electroencephalogram when each of the powers of the first and second frequency bands transition from the rest range to the exercise range
- the electroencephalogram decision method further comprising a processing step of selecting the decision condition from the plurality of conditions based on a rate of change of a border line between the rest range and the exercise range on a graph where one axis represents a power of the first frequency band and another axis represents a power of the second frequency band,
- wherein, where the second step making a decision that the electroencephalogram information represents the target electroencephalogram, the at least one of the exercise assisting step or the displaying step respectively supports the subject in his or her voluntary movement by applying the at least one of the mechanical stimulus or the electrical stimulus to the subject or displaying the image for guiding his or her voluntary movement.

11. The electroencephalogram decision method of claim 10, wherein the rate of change of the border line between the rest range and the exercise range on the graph where the one axis represents the power of the first frequency band and the another axis represents the power of the second frequency band corresponds to a slope of a decision boundary, calculated by linear discriminant analysis (LDA) method, between the rest range and the exercise range on the graph where the one axis represents the power of the first frequency band and the another axis represents the power of the second frequency band.

12. A non-transitory storage medium readable for a computer system including a processor and storing a program designed to cause the processor to carry out the electroencephalogram decision method of claim 10.

* * * * *